United States Patent [19]

Carpino et al.

[11] Patent Number: 5,101,059

[45] Date of Patent: Mar. 31, 1992

[54] AMINO ACID PROTECTING GROUPS

[75] Inventors: Louis A. Carpino, Amherst, Mass.; An-Chuu Wu, Warrington, Pa.

[73] Assignee: Research Corporation Technologies, Inc., Tucson, Ariz.

[21] Appl. No.: 446,021

[22] Filed: Dec. 5, 1989

[51] Int. Cl.$^5$ .......................................... C07D 311/82
[52] U.S. Cl. .................................. 549/388; 556/416; 556/419; 556/429; 556/440; 556/449; 558/248; 558/282; 560/27; 560/29; 560/32; 560/148; 560/155; 560/159; 560/160; 560/163; 568/808; 530/331; 530/337; 530/344; 530/345; 546/102; 546/104; 548/110; 548/253; 548/259; 548/266.1; 548/268.2; 548/336; 548/341; 548/406; 548/474; 548/525; 548/547; 549/4; 549/26; 549/214; 552/4; 552/7
[58] Field of Search ............... 530/331, 345, 337, 344; 548/110, 253, 259, 266.4, 268.2, 336, 341, 406, 474, 547; 552/4, 7; 556/416, 419, 429, 440, 449; 558/248, 282; 560/27, 29, 32, 148, 155, 159, 160, 163; 568/808; 549/214, 388

[56] References Cited

U.S. PATENT DOCUMENTS

| 3,835,175 | 9/1974 | Carpino et al. | 558/248 X |
| 3,839,396 | 10/1974 | Otsuka et al. | 552/7 X |
| 4,108,846 | 8/1978 | Meienhofer | 530/334 |
| 4,460,501 | 7/1984 | Carpino et al. | 549/27 |
| 4,818,704 | 4/1989 | Josefsson et al. | 558/282 X |

OTHER PUBLICATIONS

Carpino et al., JACS, 1970, pp. 5748-5749.
Urberg et al., Chemical Abstracts, vol 68 (1968), 25341d.
Bergmann et al., Chemical Abstracts, vol 68 (1968), 59421v.
Okabayashi et al., Chemical Abstracts, vol. 78 (1973), 58200s.
Werry et al., Chemical Abstracts, vol. 113 (1990), 58567h.
Nogradi et al., Chemical Abstracts, vol. 81 (1974), 3749j.
Negrini et al., Chemical Abstracts, vol. 95 (1981), 54559u.
Molock et al., Chemical Abstracts, vol. 98 (1983), 179191m.
Carpino et al., Chemical Abstracts, vol. 111 (1989), 233,638q.
Rigaudy et al., Chemical Abstracts, vol. 54 (1960), 5635a-b.
Simmonds et al., Chemical Abstracts, vol. 92 (1980), 22393g.

*Primary Examiner*—Richard L. Raymond
*Attorney, Agent, or Firm*—Scully, Scott, Murphy & Presser

[57] ABSTRACT

This invention relates to compounds of the formula a compound of the formula

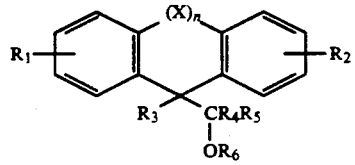

wherein
X is O, $CR_7R_8$, S or $NR_9$ wherein $R_7$ and $R_8$ are independently hydrogen, or lower alkyl, and $R_9$ is lower alkyl;
n is 0 or 1;
$R_1$ and $R_2$ are independently hydrogen, lower alkyl, monoorganosilyl, diorganosilyl, triorganosilyl, halogen, aryl, or nitro;
$R_3$ is hydrogen, lower alkyl, monoorganosilyl, diorganosilyl, triorganosilyl, halogen, 9-fluorenylalkyl, cycloalkyl, aryl or aralkyl;
$R_4$ and $R_5$ are independently hydrogen, lower alkyl, or aryl or one of $R_4$ and $R_5$ is 9-fluorenyl;
$R_6$ is H or COZ wherein Z is an amino acid, a peptide residue or a leaving group; and
with the provisos that when n is 0 and $R_3$ is hydrogen, $R_1$ and $R_2$ are not hydrogen, halogen or nitro; that when n is 0 and $R_3$ is lower alkyl, $R_1$ and $R_2$ are not hydrogen; and that when X is O or $CR_7R_8$ wherein $R_7$ and $R_8$ are H, that $R_1$, $R_2$, $R_3$, $R_4$, $R_5$, and $R_6$ are not all simultaneously H. The compounds of the present invention are useful in peptide synthesis as blocking or protecting groups for reactive groups. The present invention is also directed to a method of protecting a reactive group of an organic molecule during a reaction which modifies a portion of the molecule other than the protected group.

15 Claims, No Drawings

AMINO ACID PROTECTING GROUPS

BACKGROUND OF THE INVENTION

Support for the research leading to this invention was sponsored, in part, by the National Institute of Health. This support is gratefully acknowledged by the inventors.

A basic problem in peptide synthesis is one of blocking or protecting the amino group from interaction with a carboxyl group on the same amino acid. These undesirable side reactions are prevented by attaching to one amino acid a group that will render the $-NH_2$ group unreactive and still permit the desired reaction to take place. In addition to providing protection for the amino group, the blocking group is preferably one that can be easily removed without chemically altering the remainder of the molecule including the peptide linkage that has been built up during the synthesis. (See generally, Morrison and Boyd, *Organic Chemistry*, Third Ed., Sec. 30.10 Synthesis of Peptides, pp. 1131-1133 (1983). In addition, another basic problem in peptide synthesis is to prevent reactive side chains from undergoing unwanted reactions during coupling of amino acids.

Over the years many protecting groups have been devised. The vast majority of amino protecting groups reported for peptide syntheses have centered around three groups: carbobenzoxy (Z or Cbz; Bergmann et al. (1982) *Chem. Ber.* 65:1192), cleaved by catalytic hydrogenation; tert-butoxycarbonyl (Boc or t-Boc; Carpino (1957) *J. Am. Chem. Soc.* 79:98; ibid., 79:4427), cleaved by mild acidolysis; and 9-fluorenylmethoxycarbonyl (Fmoc; Carpino et al. (1970) *J. Am. Chem. Soc.* 92:5748), cleaved by secondary amines. These groups are orthogonal to each other because the Boc group is stable to secondary amines and hydrogenolysis, the Fmoc group is stable to acidolysis, and the Z group is stable to secondary amines and mild acidolysis. Thus, each of these protecting groups has found its place in peptide chemistry, with the Boc group being used in both solution and solid-phase syntheses, and the Z group being used generally for solution synthesis.

Presently known Fmoc and related derivatives useful as protecting groups have been described in U.S. Pat. Nos. 3,839,936; 3,835,175; and 4,108,846. The '396 patent describes Fmoc protecting groups wherein the hydrogen at the 9-position is replaced by a lower alkyl group. The '175 patent describes Fmoc and related derivatives having fused aromatic rings with halogen or nitro substituents attached to the rings. The '846 patent describes a method of using base labile N-α-amino protecting groups on amino acids during peptide synthesis. These base labile N-α-amino protecting groups include Fmoc. All the Fmoc-related compounds described in these three patents have the same advantages and disadvantages as Fmoc, namely cleavage by secondary amines like piperidine, and being of a similar solubility as Fmoc.

The search for new protecting groups in the field of peptide synthesis is still continuing especially for applications to solid phase synthetic approaches. Side reactions suffered in each cycle of a long synthesis and especially during the final step of removing all protecting groups from an assembled peptide are often serious. An ideal protecting group is one which allows removal by a specific reagent under conditions sufficiently mild that other functions are not affected.

Another problem faced when using Fmoc as a blocking group relates to the high insolubility of Fmoc amino acid derivatives, especially in inexpensive solvents. This often interferes with their use in solid phase synthesis. A protecting group which is deblocked under conditions similar to Fmoc but which exhibits higher solubility in the solvents commonly used in peptide synthesis, especially solid phase routes, is sought to facilitate solid phase synthesis.

Yet another problem results when Fmoc blocking groups are used in solution syntheses. This is the interference of by-products from the deblocking step as well as premature deblocking of Fmoc derivatives when solution syntheses need to be carried out in the presence of an excess of a base such as triethylamine, diisopropylethylamine or other mixtures of amines and solvents which effect deblocking of Fmoc. Blocking groups which form easily removable by-products, yet still share some of the advantages of Fmoc, are needed for solution synthesis.

Hence, the present invention provides chemical protecting groups, especially useful in peptide synthesis, which overcome one or more of these problems. In one instance, a new type of protecting group has been developed which exhibits most of the advantages of the base-labile, acid-stable Fmoc function but at the same time is orthogonal to the Fmoc group, i.e., requires a stronger base than piperidine for deblocking. Such a group is useful for side chain protection while the main chain is assembled via Fmoc or other compatible protection. As many of the commonly used side chain protecting groups are removed by acidolysis, the subject invention provides a process allowing peptides to be assembled without the need for treatment with acidic reagents at any stage of the synthesis. This milder general approach to peptide assembly permits the synthesis of peptides having sequences for which even trifluoroacetic acid (TFA) treatment is destructive. Hence, it is clearly valuable to be able to remove side chain protection and liberate the peptide from a support by a method other than acid treatment but yet still compatible with the use of Fmoc as an N-α-amino protecting group. One such method is to provide blocking groups which are stable to piperidine under the conditions in which Fmoc is cleaved, yet are themselves cleaved by an organic base of somewhat greater strength than piperidine. This method thus provides compounds which exhibit selective base-sensitivity in deblocking reactions and can obviate the need for acid treatment during peptide synthesis.

SUMMARY OF THE INVENTION

This invention relates to compounds for use as blocking groups to protect reactive substituents of amino acids and other organic molecules from side reactions during chemical reactions. In particular, this invention is especially useful for protecting reactive groups of amino acids during peptide synthesis, including N-α-amino groups and side chain amino, hydroxyl and acid (e.g., carboxyl) groups. One subclass of these compounds provides protecting groups which are orthogonal to the Fmoc protecting group, i.e., when used as protecting groups, these compounds are stable to cleavage by piperidine under conditions in which Fmoc is cleaved but can still be cleaved by stronger bases. In contrast to the typical Fmoc/tBoc strategy of peptide synthesis, requiring acid treatment to remove side chain protecting groups, when the subject compounds which are orthogonal to Fmoc are used as side chain protecting groups, then there is no need for acid treatment. Hence, the present invention enables synthesis of acid-sensitive peptides. A second subclass of the subject compounds provides protecting groups which are more soluble in the solvents routinely used in peptide synthesis than is Fmoc and, hence, provides a valuable and more efficient alternative to the Fmoc group for peptide synthesis. Many of these compounds are also less expensive. Moreover, some of the compounds have by-products which are more easily detected than those from Fmoc, e.g., the reactions can be monitored spectrophotometrically, making it easier to determine when reactions are completed.

The compounds of the present invention are represented by formula I:

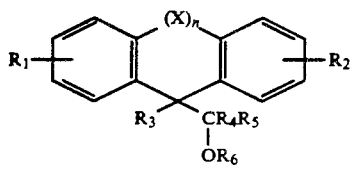

wherein

X is O, $CR_7R_8$, S or $NR_9$ wherein $R_7$ and $R_8$ are independently hydrogen, or lower alkyl, and $R_9$ is lower alkyl;

n is 0 or 1;

$R_1$ and $R_2$ are independently hydrogen, lower alkyl, monoorganosilyl, diorganosilyl, triorganosilyl, halogen, aryl, or nitro;

$R_3$ is hydrogen, lower alkyl, monoorganosilyl, diorganosilyl, triorganosilyl, halogen, 9-fluorenylalkyl, cycloalkyl, aryl or aralkyl;

$R_4$ and $R_5$ are independently hydrogen, lower alkyl, aryl or one of $R_4$ and $R_5$ is 9-fluorenyl;

$R_6$ is H or COZ wherein Z is an amino acid, a peptide residue or a leaving group; and with the provisos that when n is 0 and $R_3$ is hydrogen, R and $R_2$ are not hydrogen, halogen or nitro; that when n is 0 and $R_3$ is lower alkyl, $R_1$ and $R_2$ are not hydrogen; and that when X is O or $CR_7R_8$ wherein $R_7$ and $R_8$ are H, that $R_1$, $R_2$, $R_3$, $R_4$, $R_5$, and $R_6$ are not all simultaneously H.

The preferred compounds of the invention are 9-xanthenylmethyl derivatives, 9,10-dihydroanthracene derivatives, 9-(9'-fluorenylmethyl)fluorenylmethyl derivatives and 9-triorganosilyl-fluorenylmethyl derivatives as represented by Formula I.

As embodied and broadly described herein, the invention is also directed to a method of protecting a reactive group of an organic molecule during a reaction which modifies a portion of the molecule other than the protected group. The method involves (a) reacting the reactive group with a compound of formula I thereby forming a protected group on the molecule, (b) modifying a portion of the molecule other than the protected group by chemical reaction, and (c) removing the protecting group.

In preferred embodiments, the chemical reaction is formation of a peptide bond or protection of a second reactive group on an amino acid. The preferred reactive groups are amino, hydroxy and carboxy groups on amino acid side chains or N-α-amino groups.

Another aspect of the invention is directed to a method of peptide synthesis, either in solution or by solid phase, using at least one amino acid having a protecting group in accordance with a compound of formula I.

A still further aspect of the invention is directed to an improved method of peptide synthesis wherein at least one amino acid has a side chain protecting group which exhibits selective base-sensitivity in deblocking reactions, wherein said side chain protecting group is stable to removal by piperidine under conditions where piperidine normally removes the Fmoc group from an N-α-Fmoc protected amino acid or peptide, and is removed by a base of greater strength than piperidine under similar conditions. The preferred amino acid side chain protecting groups are represented by formula II:

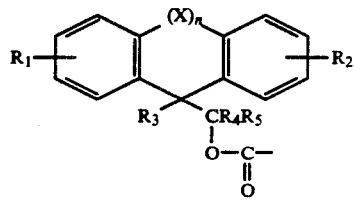

wherein

X is O, $CR_7R_8$, S or $NR_9$ wherein $R_7$ and $R_8$ are independently hydrogen or lower alkyl, and $R_9$ is lower alkyl;

n is 0 or 1;

$R_1$ and $R_2$ are independently hydrogen, lower alkyl, substituted silyl, aryl, deuterium or an electron releasing group;

$R_3$ is hydrogen, lower alkyl, monoorganosilyl, diorganosilyl, triorganosilyl, halogen, 9-fluorenylmethyl, cycloalkyl, aryl or aralkyl;

$R_4$ and $R_5$ are independently hydrogen, lower alkyl, aryl or one of $R_4$ and $R_5$ is 9-fluorenyl;

with the provisos that when n is 0 and $R_3$ is hydrogen or lower alkyl, $R_1$ and $R_2$ are not hydrogen; and that when n is 0 and $R_3$ is triorganosilyl, the triorganosilyl is not trimethylsilyl.

DETAILED DESCRIPTION OF THE INVENTION

This invention relates to compounds for use as blocking groups to protect reactive substituents of amino acids and other organic molecules from side reactions during chemical reactions. In particular, this invention is especially useful for protecting reactive groups of amino acids during peptide synthesis, including N-α-amino groups and side chains amino, hydroxyl and acid (e.g., carboxyl) groups. One subclass of these compounds provides protecting groups which are orthogonal to the Fmoc protecting group, i.e., when used as protecting groups, these compounds are stable to cleavage by piperidine under conditions in which Fmoc is cleaved but can still be cleaved by stronger bases. Moreover, like Fmoc, these compounds are generally stable to mild acidolysis and catalytic hydrogenation. A second subclass of the subject compounds provide protecting groups which are more soluble in the solvents used in peptide synthesis, cheaper, or have by-products which are easier to detect, e.g., by U.V. analysis, than Fmoc and, hence, provides another valuable and efficient alternative to using the Fmoc group in peptide synthesis.

Protecting groups in the first category include derivatives of the 9-xanthenylmethyl (XM) function, derivatives of dihydroanthracene (DHA), derivatives of the 9-(9'-fluorenylmethyl)fluorenylmethyl function (9-FM²) and some derivatives of the triorganosilyl Fmoc [(R)₃Si-FM] compounds. Each of these compounds has particular advantages and are represented below by structures A-D, respectively.

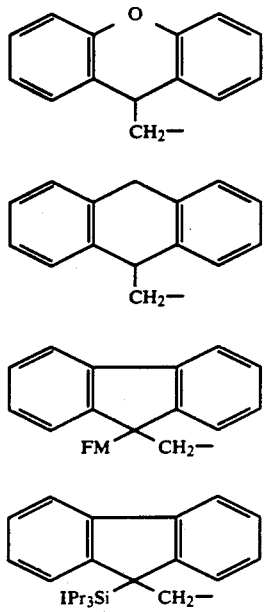

All systems derived from A(XM), B(DHA) and D (R₃Si-FM) are easily synthesized from inexpensive, commercially available intermediates. System C (9-FM²) has excellent properties but the synthetic route to the key alcohol is not as simple as for the other three cases. Systems derived from A, B and C are totally stable to acidic reagents, a property they share with the Fmoc system.

Surprisingly, it was discovered that systems such as D fit in two categories. In general these silyl derivatives exhibit variable stability to acid, yet they are still useful as a replacement to Fmoc or as protecting groups which are orthoganal to Fmoc by virtue of their selective base sensitivity. Some trisubstitutedsilyl-Fmoc systems are sensitive to piperidine but show greater solubility than Fmoc in the solvents used for peptide synthesis. Other trisubstitutedsilyl-Fmoc compounds resist cleavage by piperidine but can still be cleaved by treatment with a stronger base.

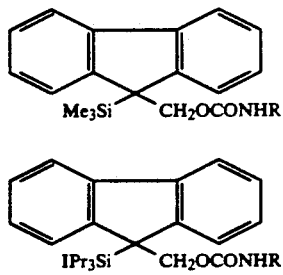

For example, the trimethylsilyl-Fmoc (9-TMS-Fmoc), represented by derivative E, is deblocked by piperidine, although somewhat more slowly than the Fmoc group itself. The 9-TMS function interferes greatly with crystal packing and is enormously more soluble in non-polar solvents than ordinary Fmoc analogs. As an illustration, 9-TMS-Fmoc-NHC₆H₄Cl-p is soluble to the extent of 53 g/100 mL in CH₂Cl₂ which is 16 times that of the Fmoc analog. Moreover, the solubility of the other protecting groups provided by the present invention should also be enhanced by the use of a 9-trimethylsilyl-substituent as demonstrated in the Fmoc case.

Hence, 9-TMS-Fmoc can be used as a highly solubilizing equivalent for Fmoc in normal peptide syntheses. All by-products are exactly the same as for the Fmoc case except for the TMS derivative of piperidine which is still washed out with all other by-products.

In contrast, the more hindered triisopropylsilyl (TIPS) analog of Fmoc, represented by derivative F, is stable to piperidine but cleaved by the inorganic base, fluoride ion. Hence, the TIPS analog is orthogonal to Fmoc, Z and tBoc and, thus, is useful as a side chain protecting group, especially when Fmoc is used to protect the α-amino group of an amino acid.

The 2,7-dichloro derivatives of the Xmoc function are of special interest. During the course of these studies, it was discovered that whereas the Xmoc group is stable to piperidine, the 2,7-dichloro analog of Xmoc is deblocked by piperidine as easily as the Fmoc group. This compound has the advantage of greater solubility than Fmoc derivatives, and a further advantage that its dibenzofulvene by-product is a stable compound unlike the Fmoc dibenzofulvene by-product which polymerizes. This latter property is particularly important when peptide synthesis is carried out in solution. Hence, 2,7-dichloro-9-xanthenylmethyl protecting groups can be used for the same purposes as Fmoc, i.e., as an N-α-amino protecting group which is readily cleaved from an amino acid by a simple amine like piperidine. Related compounds having electron withdrawing groups (halogen groups, nitro groups and the like) on the fused aromatic rings share these properties.

Accordingly, the present invention is directed to compounds of the formula I:

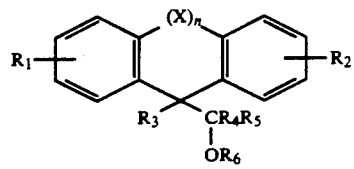

wherein
X is O, CR₇R₈, S or NR₉ wherein R₇ and R₈ are independently hydrogen, or lower alkyl, and R₉ is lower alkyl:

n is 0 or 1;

R₁ and R₂ are independently hydrogen, lower alkyl, monoorganosilyl, diorganosilyl, triorganosilyl, halogen, aryl, or nitro;

R₃ is hydrogen, lower alkyl, monoorganosilyl, diorganosilyl, triorganosilyl, halogen, 9-fluorenylalkyl, cycloalkyl, aryl or aralkyl;

R₄ and R₅ are independently hydrogen, lower alkyl, aryl or one of R₄ and R₅ is 9-fluorenyl;

R₆ is H or COZ wherein Z is an amino acid, a peptide residue or a leaving group; and with the provisos that when n is 0 and R₃ is hydrogen, R and R₂ are not hydrogen, halogen or nitro; that when n is 0 and R₃ is lower alkyl, R₁ and R₂ are not hydrogen;

and that when X is O or CR₇R₈ wherein R₇ and R₈ are H, that R₁, R₂, R₃, R₄, R₅, and R₆ are not all simultaneously H.

As used herein, the terms lower alkyl, when used singly or in combination, refer to alkyl groups containing one to six carbon atoms. They may be straight chain or branched and include such groups as methyl, ethyl, propyl, isopropyl, butyl, sec-butyl, isobutyl, t-butyl, pentyl, isopentyl, neopentyl, hexyl and the like. The preferred alkyl groups contain one to four carbon atoms.

The term aryl, when used alone or in combination, refer to an aromatic ring containing six to ten ring carbon atoms. The aryl group includes phenyl, and 1- or 2-naphthyl. The preferred aryl group is phenyl.

The term aralkyl refers to aryl groups as described above which have alkyl groups as ring substituents. The most preferred aralkyl group is benzyl.

The term organo of monoorgano, diorgano or triorganosilyl as used herein refers to hydrocarbon groups which are bonded to a central silane atom. The remaining valencies of these hydrocarbon groups include lower alkyl and aryl groups as defined hereinabove. The preferred silyl groups are triorganosilyl groups wherein the organo groups are independently methyl, phenyl or isopropyl groups. These organo groups are also preferred when monoorgano or diorganosilyl groups are employed.

When n is zero, the preferred compounds of this invention are those wherein R₃ is triorganosilyl or 9-fluorenylalkyl. Especially preferred triorgano derivatives are those wherein R₃ in trimethylsilyl (as a protecting group similar to Fmoc) and triisopropylsilyl (as a protecting group orthogonal to Fmoc). An especially preferred 9-fluorenylalkyl group is 9-fluorenylmethyl.

When n is one, preferred X groups of the present invention are O (oxygen) or CR₇R₈, wherein R₇ and R₈ are as defined hereinabove. Especially preferred X groups are O and CH₂.

Preferred compounds of the present invention are those wherein R₄ and R₅ are both hydrogen or wherein at least one of R₄ and R₅ is hydrogen and the other is 9-fluorenyl. Preferred substituents for R₁ and R₂ are hydrogen; triorganosilyl, especially trimethylsilyl; lower alkyl, especially methyl and t-butyl; and halogen, especially chlorine and bromine.

When compounds of the present invention are used to protect a reactive group and introduce a compound of Formula I, Z is a leaving group. As is generally known in the art and for the purposes of the present invention "a leaving group" is defined as a group which is readily broken away from its union with a carbon atom. It is one which readily joins, for example, with an active hydrogen atom to split out a compound containing the hydrogen atom and the leaving group. Leaving groups are generally electron attracting groups either because of their electronegativity or because they have an inductive effect. Leaving groups are further defined in U.S. Pat. No. 4,394,519 to Carpino et al. which is incorporated herein by reference.

The preferred leaving groups Z are halo, CN, SR₁₀, SAr, N₃, OAryl,

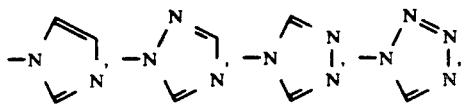

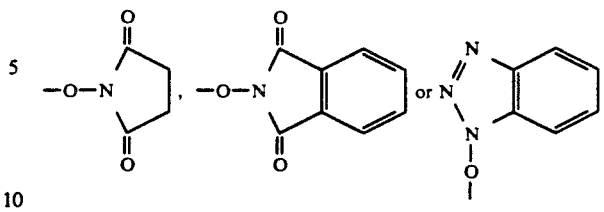

wherein R₁₀ is lower alkyl, aryl or aralkyl, wherein the alkyl or aryl groups are unsubstituted, or mono- or disubstituted with halides, SO₂R₁₁, SOR₁₁, COOR₁₁, COR₁₁, CHO, CN, CF₃ or NO₂ and R₁₁ is lower alkyl or aryl.

The most preferred leaving groups are halo, especially Cl and Br.

When Z is an amino acid residue or a peptide residue it becomes part of a stable system at least during chemical reactions involved in peptide bond formation or other reactions involved in peptide bond formation or other reactions to protect other reactive groups on the amino acid or peptide. An amino acid residue is defined herein as an amino acid or derivative thereof, such as an ester and the like, minus an amine hydrogen on the amino end of the molecule. A peptide residue is a peptide of two or more amino acids or derivatives thereof, such as an ester and the like, linked through an amide bond and it contains one less amino hydrogen on the amino end of the peptide.

In a preferred embodiment Z is an alpha-amino acid.

The alpha-amino acids ar those which are well known to one skilled in the art. These amino acids, e.g., the naturally occurring alpha-amino acids, are often used in the chemical synthesis of peptides. These amino acids include alanine, arginine, asparagine, aspartic acid, cysteine, cystine, glutamic acid, glutamine, glycine, histidine, hydroxylysine, hydroxyproline, isoleucine, leucine, lysine, methionine, norleucine, phenylalanine, proline, serine, threonine, tryptophan, tyrosine, valine, penicillamine, and the like.

In general, preferred compounds may have any combination of one or more of the preferred groups (i.e., R₁-R₁₁) of the invention.

The especially preferred compounds of the invention wherein Z is a leaving group are listed below:
9-xanthenylmethyl chloroformate
9-xanthenylmethyl azidoformate
succinimidyl 9-xanthenylmethyl carbonate
2,7-dichloro-9-xanthenemethanol
9-trimethylsilyl-9-fluorenemethanol
9-trimethylsilyl-9-fluorenylmethyl chloroformate
9-dimethyl(phenyl)silyl-9-fluorenylmethyl benzyl ether
9-diphenyl(methyl)silyl-9-fluorenylmethyl benzyl ether
9-triphenylsilyl-9-fluorenylmethyl benzyl ether
9-dimethyl(phenyl)silyl-9-fluorenemethanol
9-diphenyl(methyl)silyl-9-fluorenemethanol
9-trisopropylsilyl-9-fluorenemethanol
2,7-bis(trimethylsilyl)-9-fluorenemethanol
2,7-bis(trimethylsilyl)-9-fluorenylmethyl chloroformate
2,7-di(t-butyl)-9-trimethylsilyl-9-fluorenylmethyl benzyl ether
9(9'-fluorenylmethyl)-9-fluorenylmethyl benzyl ether
9(9'-fluorenylmethyl)-9-fluorenemethanol bis(9-fluorenyl)methyl chloroformate The above compounds are useful in preparing amino acid derivatives having the corresponding protecting group.

The compounds of the invention represented by Formula I wherein Z is a leaving group are prepared by art recognized methods. For instance, the alcohol series, i.e., wherein $R_6$ is H, may be synthesized as shown in Scheme I:

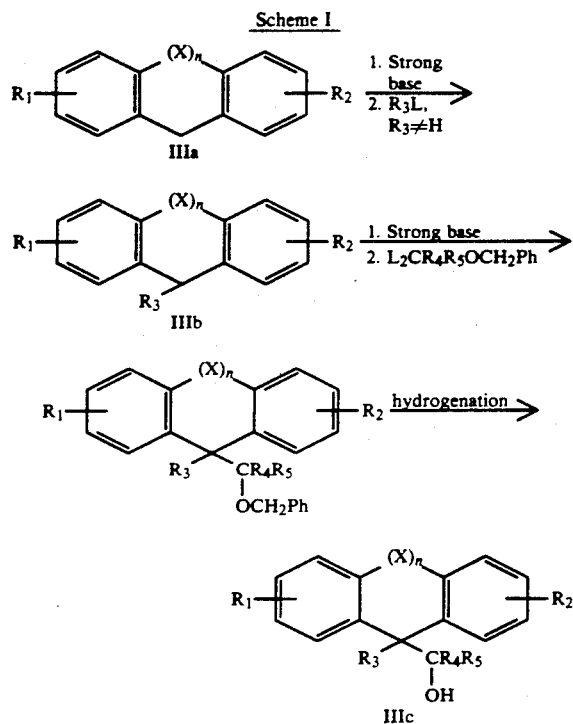

In general, to introduce $R_3$ groups (except when $R_3$ is H) compound IIIa is treated with a strong base and then reacted with $R_3L_1$, wherein $L_1$ is a leaving group such as halogen, tosylate, mesylate and the like, to yield IIIb. To introduce the alcohol moiety, IIIb is treated with a strong base and converted to the alkylbenzyl ether derivative by reaction with $L_2CR_4R_5OCH_2Ph$ and then reduced to the corresponding alcohol IIIc by hydrogenation in the presence of a palladium-charcoal catalyst. $L_2$ is leaving group and defined as for $L_1$.

In both steps of the above reaction n-butyl lithium and the like are suitable strong bases.

When $R_3$ is H, the carboxylic acid IIId can be reduced to the corresponding alcohol IIIc by treatment with a reducing agent such as lithium aluminum hydride.

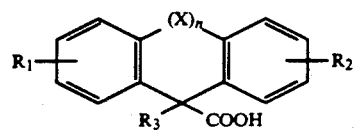

IIId

As an example, the alcohols of the 9-triorganosilyl derivatives of Fmoc are prepared according to Scheme I. In this case, the desired alcohol is obtained by introducing the triorganosilyl group (as $R_3$) via reaction of fluorene with the triorganosilylhalide in the presence of n-butyl lithium and an inert solvent. These compounds are converted to the 9-benzylmethyl ether derivatives by reaction with chloromethyl benzyl ether in the presence of n-butyl lithium and an inert solvent. Finally, the corresponding benzyl methyl ethers are reduced to yield the appropriate alcohol. Reduction can be accomplished by hydrogenation in the presence of a palladium-charcoal catalyst. To prepare the 9-triisopropylsilyl-9-fluorene- methanol, fluorene can be derivatized with the corresponding silyl and then converted directly to the methanol by hydromethylation with gaseous formaldehyde.

Further, alkyl groups can be introduced specifically at the 9-position of IIId by converting the carboxylate to an ester and then reacting the ester with the appropriate alkyl halide in the presence of sodium methoxide and an inert solvent. The alcohol can then be obtained by reduction with lithium aluminum hydride. The 9-fluorenyl derivatives of IIIb are prepared by the same method using 9-halofluorenes.

The 9-(9'-fluorenylmethyl)fluorenemethanol compounds can be prepared by reducing the benzyl ether derivative of bis(9-fluorenyl)methane. The benzyl ether moiety is introduced onto this molecule by the reaction shown in Scheme I.

Moreover, alkyl groups can be introduced onto fused aromatic rings, especially at the 2 and 7 positions, by Friedel-Crafts alkylation of IIIa with an alkyl halide. These compounds are then converted to the corresponding alcohols, for example, by deprotonation and acylation with sodium hydride and ethyl formate to produce an aldehyde at the 9-position. The aldehyde is reduced to give the desired alcohol.

An example of a reaction scheme to prepare 2,7-bis(-triorganosilyl) substituted compounds of formula IIIa is exemplified in Scheme II which shows the synthesis of 2,7-bis(trimethylsilyl)fluorenemethanol.

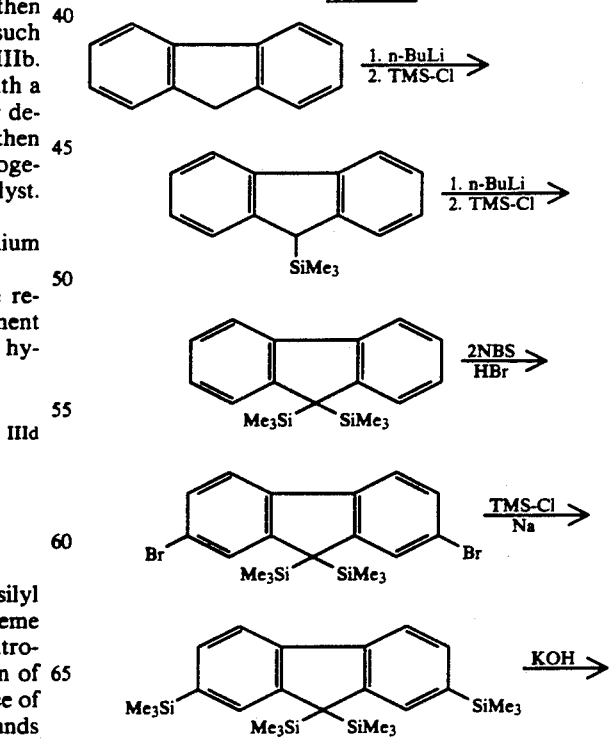

-continued
Scheme II

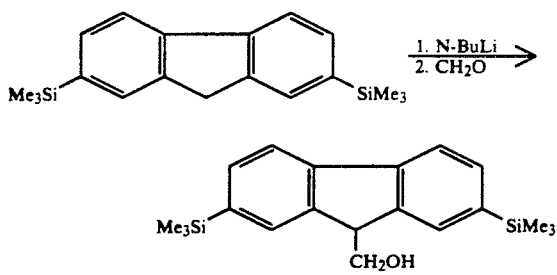

By this method, IIIa compounds are deprotonated by n-butyl lithium, silated at the 9-position by the appropriate triorganosilylhalide and the procedure repeated to obtain the 9,9-bis(triorganosilyl) derivative which is then brominated to afford the 2,7-dibromo-9,9-bis(triorganosilyl) derivative. This latter derivative is converted to the corresponding 2,7,9,9-tetrakis(triorganosilyl) by treating with a triorganosilylhalide in the presence of sodium metal. Next, the 9-position triorganosilyl groups are removed by refluxing in an alcoholic solution of 10% potassium hydroxide to yield the desired 2,7-bis(triorganosilyl) derivatives of IIIa. Finally, the corresponding alcohols can be prepared by hydroxymethylation with gaseous formaldehyde.

Typically, the reactions for synthesis of the compounds described for preparing the alcohols IIIc are carried out in an inert organic solvent. Suitable solvents include alcohols such as methanol, ethanol, isopropanol, t-butanol and the like, ethers such as diethyl ether, 1,4-dioxane, tetrahydrofuran (THF) and the like, hydrocarbons such as benzene, hexane, cyclohexane, toluene, Skelly solvents and the like, and halogenated hydrocarbons such as CHCl$_3$, CCl$_4$, CH$_2$Cl$_2$ and the like.

Temperatures for these reactions range from about −78° C. to the reflux temperature of the solvent being employed. Unless indicated to the contrary in the discussion of the various reaction schemes described hereinabove and hereinafter, the preferred temperatures are from about 0° C. to about 100° C.

The compounds of the present invention having Formula I with R$_6$ being COZ as a leaving group (Compound IV) can be prepared from the alcohols IIIc obtained as described herein. In this instance, a compound of the Formula IV can be prepared as illustrated in Scheme III:

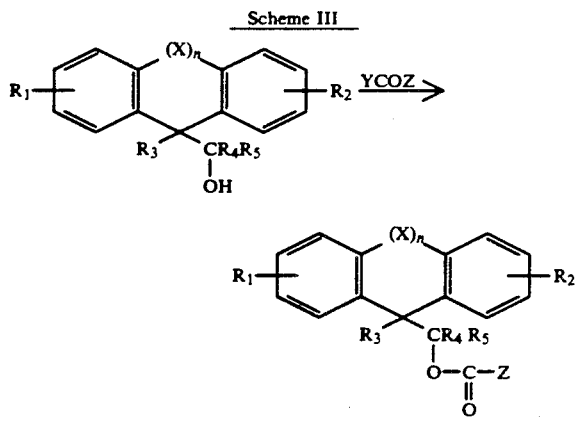

Scheme III or by Scheme IV

Scheme IV

-continued

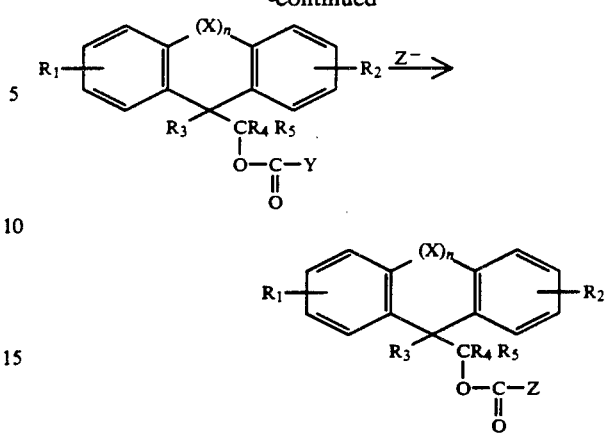

wherein Y is a better leaving group than Z. Typically Y can be a halogen, cyano, azido, tosylate or other leaving group as herein defined, especially F or Cl. Since Y is defined to be a better leaving group than Z, and Z must be a group as herein defined, one skilled in the art can readily select Y and Z such that Y is a better leaving group than Z. In other words, in Scheme IV Y must be a group which can be preferentially displaced by Z. Likewise in Scheme III, Y abstracts the hydrogen of the alcohol to form HY and the desired product. As one skilled in the art knows, any combination of the leaving groups as herein defined can be used for Y and Z provided that Y is the better leaving group of the two substituents.

Typically, reactions such as indicated by Scheme III are carried out in an inert organic solvent. As defined herein an inert solvent is a reaction inert solvent, i.e., one which will not react with the reagents or reactants under the given reaction conditions. Suitable solvents are halogenated or non-halogenated hydrocarbons containing up to about eight carbon atoms, e.g., methylene chloride, ethylene dichloride, benzene, isooctane and the like. Reactions are conducted at temperatures of from about 0° C. to about 25° C. during a reaction period of from about 1 to about 6 hours. Suitable yields are obtained with equimolar quantities of reactants, although the yield may often be appreciably increased by utilizing an excess of either one of them, for example, up to about a 20% molar excess. Generally speaking, the halogen substituted compounds are prepared under less rigorous reaction conditions than are required for the preparation of those compounds wherein the substituent is of higher molecular weight. The presence of a weak base may increase the rate of reaction.

Reactions of Scheme IV in which the substituent placed on the carbonyl carbon atom is initially present in an ionic form are carried out in inert polar organic solvents which will enhance ionization, including, for example, acetonitrile, dimethylformamide, dimethylsulfoxide, tetrahydrofuran, dioxane and the like. The reaction is normally carried out at a temperature of from about 0° C. to about 25° C. during a period of from about 1 to 5 hours. Preferably equimolar quantities of reactants are employed to minimize side reactions but a moderate excess of either reactant would not introduce appreciable difficulties.

The compounds described hereinabove can be used to protect reactive groups, especially primary and secondary amines and hydroxyl groups, and more especially reactive groups of amino acids. In fact, an embodiment of the present invention is directed to a method of protecting a reactive group on an organic molecule during a reaction which modifies a portion of the molecule other than the reactive group, having the steps of:

a) reacting the reactive group with a compound of the formula

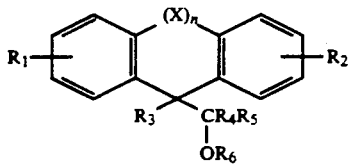

wherein

X is O, $CR_7R_8$, S or $NR_9$ wherein $R_7$ and $R_8$ are independently hydrogen, or lower alkyl, and $R_9$ is lower alkyl;

n is 0 or 1;

$R_1$ and $R_2$ are independently hydrogen, lower alkyl, monoorganosilyl, diorganosilyl, triorganosilyl, halogen, aryl, or nitro;

$R_3$ is hydrogen, lower alkyl, monoorganosilyl, diorganosilyl, triorganosilyl, halogen, 9-fluorenylalkyl, cycloalkyl, aryl or aralkyl;

$R_4$ and $R_5$ are independently hydrogen, lower alkyl, aryl one of $R_4$ and $R_5$ is 9-fluorenyl;

$R_6$ is H or COZ wherein Z is a leaving group; and with the provisos that when n is 0 and $R_3$ is hydrogen, $R_1$ and $R_2$ are not hydrogen, halogen or nitro; that when n is 0 and $R_3$ is lower alkyl, $R_1$ and $R_2$ are not hydrogen; and that when X is O or $CR_7R_8$ wherein $R_7$ and $R_8$ are H, that $R_1$, $R_2$, $R_3$, $R_4$, $R_5$, and $R_6$ are not all simultaneously H, thereby forming a protected molecule having a protected reactive group;

(b) modifying the portion of the molecule other than the protected reactive group by chemical reaction; and (c) deprotecting the protected reactive group.

The compounds described hereinabove are useful in protecting reactive groups during synthesis of organic molecules including bioorganic molecules, e.g., peptides and polypeptides, nucleotides and polynucleotides.

An application of the present invention is using the compounds described herein wherein Z is a leaving group to protect the amino group of an amino acid during peptide synthesis. Another application of this invention is to protect reactive group(s) on the side chain of an amino acid. In this case, the chemical reaction may be the protection of a second reactive group on the amino acid or it may be the reaction to form a peptide bond. Therefore, the present invention is also directed to the method for the preparation of a peptide which comprises:

(a) reacting a first amino acid having a free reactive group with a compound of the formula:

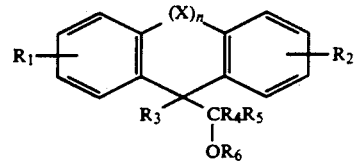

wherein

X is O, $CR_7R_8$, S or $NR_9$ wherein $R_7$ and $R_8$ are independently hydrogen or lower alkyl, and $R_9$ is lower alkyl;

n is 0 or 1;

$R_1$ and $R_2$ are independently hydrogen, lower alkyl, monoorganosilyl, diorganosilyl, triorganosilyl, halogen, aryl, or nitro;

$R_3$ is hydrogen, lower alkyl, triorganosilyl, halogen, 9-fluorenylalkyl, cycloalkyl, aryl or aralkyl;

$R_4$ and $R_5$ are independently hydrogen, lower alkyl, aryl or one of $R_4$ and $R_5$ is 9-fluorenyl;

$R_6$ is H or COZ wherein Z is a leaving group; and with the provisos that when n is 0 and $R_3$ is hydrogen, $R_1$ and $R_2$ are not hydrogen, halogen or nitro; that when n is 0 and $R_3$ is lower alkyl, $R_1$ and $R_2$ are not hydrogen; and that when X is O or $CR_7R_8$ wherein $R_7$ and $R_8$ are H, that $R_1$, $R_2$, $R_3$, $R_4$, $R_5$, and $R_6$ are not all simultaneously H, thereby introducing a protecting group onto the first amino acid (b) reacting the product of (a) with an amino acid or peptide having a free amino group; and (c) removing the protecting group. Optionally, this method includes a further step of reacting the product of (a) with an additional protecting group before carrying out step (b). In a typical embodiment, this method is included at least once as one cycle in peptide synthesis in which an amino acid is added to a growing peptide chain.

Thus, in the most preferred embodiment, compounds of the present invention can be used as blocking groups for amino acids during peptide synthesis by either solution or solid phase methods. The preferred amino acids are alpha-amino acids.

More specifically, the compounds of Formula I wherein Z is a leaving group, can react with a carboxy-protected amino acid (Vb) as indicated in Scheme V:

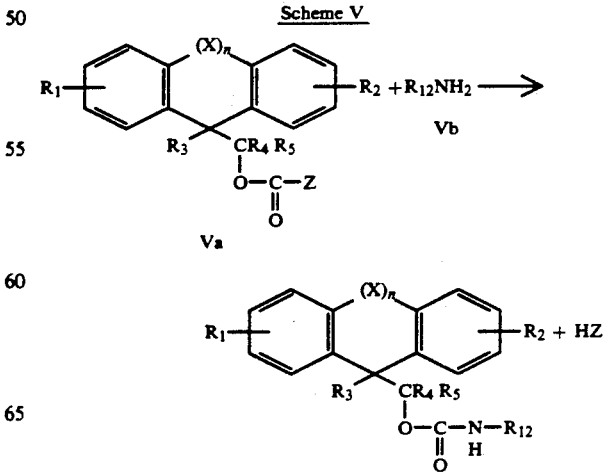

In the above scheme, X, n, $R_1$–$R_8$, and Z are as defined above, and $R_{12}NH_2$ (Vb) is an alkyl amine, aryl amine or an amino acid. Examples of amines are aniline, p-chloroaniline and the like. The amino acids are the alpha amino acids described hereinabove and include phenylalanine, glycine, valine, and the like. Often the amino acids are protected by a carboxy protecting group known in the art.

A variety of carboxy protecting groups known in the art may be employed. Examples of many of these possible groups may be found in "Protective Groups in Organic Synthesis" by T. W. Green, John Wiley and Sons, 1981. The preferred carboxy protecting group is the t-butyl ester.

In scheme V, a compound of Formula Va is reacted with a carboxy protected amino acid Vb to form Vc which is then hydrolyzed in acid to form a compound of Formula I wherein Z is an amino acid adduct. The most preferred protecting groups are Xmoc, DHAmoc, 9-FM-Fmoc and 9-$(R)_3$Si-Fmoc and their derivatives prepared in accordance with the subject invention.

If the leaving group is a halogen, especially chlorine, the reaction may be effected in an inert, polar organic solvent such as dioxane, tetrahydrofuran, dimethylformamide, pyridine or other solvent containing, for example, up to eight carbon atoms. The reaction is run under alkaline conditions, typically dilute aqueous alkali metal base such as sodium or potassium hydroxide or carbonate, at low temperatures, for example, from about 0° C. to 25° C. during a period of from about 2 to 3 hours. Usually the protected amino acid or peptide will precipitate upon acidification of the mixture, and may be purified by any appropriate method such as recrystallization. Excess blocking reagent may be employed, even up to 0.5 molar excess, but equimolar quantities of reactants generally give better results.

Alternatively, the methods known in the art are used for specifically coupling amino acid side chains to protecting groups. For example, to specifically couple a protecting group to the epsilon amino group of lysine, the amino acid is complexed with copper prior to conducting the coupling reaction. After coupling, the copper is removed by chelation with EDTA and the N-ε-protected lysine is recovered as a precipitate and purified by recrystallization.

The protected amines can also be prepared by reaction of the Formula I alcohols with isocyanates. This reaction will form the Formula I, especially XM, DHA, 9-$FM_2$ and 9-$(R)_3$Si-FM, carbamates of amino acids directly without requiring the conversion of the alcohols to chloroformate.

Another aspect of the invention is directed to an improved method of peptide synthesis wherein at least one amino acid has a side chain protecting group which exhibits selective base-sensitivity in deblocking reactions, wherein said side chain protecting group is stable to removal by piperidine under conditions where piperidine normally removes the Fmoc group from an N-α-Fmoc-protected amino acid or peptide, and wherein said side chain protecting group is removed by a base of greater strength than piperidine. Most of these compounds are also stable to mild acidolysis, e.g., treatment with TFA, and catalytic hydrogenolysis. Peptide synthesis may be conducted as described herein and may be by solution or solid phase methods.

As used herein, selective base-sensitivity in deblocking reactions is defined to be the differential stability of a protecting group with respect to its removal under similar reaction conditions by treatment with one or more bases. Selective base-sensitivity is another method of deblocking which is orthogonal to the methods of deblocking Fmoc, Z or tBoc protecting groups. Thus, under a particular reaction condition, the protecting group is stable to removal by certain bases, whereas treatment with other stronger bases causes the protecting group to be removed under the same (or similar) reaction conditions. In addition to the relative strength of the bases, the conditions and duration of contact with the base are also important in defining selective base-sensitivity. Thus, for this invention the side chain protecting groups exhibit selective base-sensitivity such that these groups are stable to removal by piperidine under conditions, including duration of time, needed to normally remove an Fmoc group from an N-α-Fmoc protected amino acid or peptide, yet the subject groups can be removed under appropriate reaction conditions by bases stronger than piperidine. While sensitivity of a protecting group relative to two bases is defined under similar reaction conditions, one skilled in the art recognizes that the actual deblocking reaction need not be performed under those exact conditions. One skilled in the art can determine the relative base sensitivity of the subject protecting groups using the methods detailed in the examples. Examples of bases which remove the subject groups are described in the section entitled *Cleavage of the Protecting Group* (below).

The preferred protecting groups are represented by compounds of formula II:

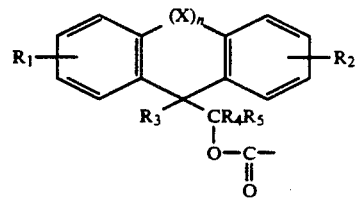

wherein
X is O, $CR_7R_8$, S or $NR_9$ wherein $R_7$ and $R_8$ are independently hydrogen or lower alkyl, and $R_9$ is lower alkyl;

n is 0 or 1;

$R_1$ and $R_2$ are independently hydrogen, lower alkyl, substituted silyl, aryl, deuterium or an electron releasing group;

$R_3$ is hydrogen, lower alkyl, monoorganosilyl, diorganosilyl, triorganosilyl, halogen, 9-fluorenylmethyl, cycloalkyl, aryl or aralkyl;

$R_4$ and $R_5$ are independently hydrogen, lower alkyl, aryl or one of $R_4$ and $R_5$ is 9-fluorenyl;

with the provisos that when n is 0 and $R_3$ is hydrogen, $R_1$ and $R_2$ are not hydrogen, halogen or nitro; that when n is 0 and $R_3$ is lower alkyl, $R_1$ and $R_2$ are not hydrogen; and that when n is 0 and $R_3$ is triorganosilyl, the triorganosilyl is not trimethylsilyl.

Unless otherwise described below, the terms for defining the various R groups are as hereinbefore defined and the preferred compounds have the preferred R groups described before provided they are in accordance with formula II.

$R_1$ and $R_2$ are additionally defined to be a substituted silyl, deuterium or an electron releasing group. As used herein substituted silyl refers monoorgano, diorgano or triorganosilyls as hereinbefore defined, and further includes other organo substituents as alkoxy such that the substituted silyl retains its ability to act as an electron releasing group. By electron releasing group is meant a ring substituent which increases the electronegativity of the aromatic ring. Examples of electron releasing groups are alkyl, substituted silyl, alkoxy groups and the like. Especially preferred groups of the invention include methyl, t-butyl, and triorganosilyl groups. One skilled in the art, moreover, knows that the selected electron releasing groups must be inert to subsequent chemical reactions when a compound with that group is used as a protecting agent.

In this context electron releasing groups act to slow removal of protecting groups of Formula II by piperidine whereas electron withdrawing groups act to enhance or at least maintain the ability of piperidine to remove the subject protecting groups. Aryl groups tend to stabilize the protecting groups of Formula II through resonance effects.

PREPARATION OF PEPTIDES

The carbonyl group of the protecting groups in accordance with Formula I once placed on an amino function which is to be protected is especially stable. This makes it possible to use a variety of methods for forming peptides, both in solution and by solid phase, without danger of cleavage of the protecting group. In fact, the subject protecting groups are generally stable under acidic conditions, such as using hydrogen bromide or chloride in various organic solvents, or trifluoroacetic acid, involved in the removal of most of the commonly used protecting groups. As provided herein, the special advantages of the particular compounds of this invention greatly increase the options available to the skilled peptide chemist for the preparation of complex polypeptides. The present invention is thus directed to a method of peptide synthesis which provides that at least one amino acid be protected by a group in accordance with Formula I (i.e., with Z being an amino acid). Accordingly, the other amino acids may be protected by any of the usual protecting or blocking groups known to one skilled in the art.

For coupling an N-α-protected amino acid or peptide with a free amino group of another amino acid or peptide to produce di-, tri-, and higher oligopeptides, any of a wide variety of procedures are available. Generally speaking, most of the coupling procedures normally employed by the skilled practitioner can be used. For example, a carboxy protected amino acid can be reacted with an amino-protected amino acid under peptide forming conditions, i.e., amide forming conditions, in the presence of a coupling agent such as dicyclohexylcarbodiimide (DCC). In this way, amino acids can be added to the chain sequentially until the desired peptide is synthesized.

The use of activated esters, suitable aryloxy or thioaryl esters, especially substituted phenyl esters such as p-nitrophenyl or pentafluorophenyl esters, also leads to satisfactory results.

One coupling procedure which is especially favored is to convert the free carboxy end of the protected amino acid or peptide into an N-hydroxy succinimide or 1-hydroxybenzotriazole (HOBt) ester. This may be accomplished by using dicyclohexylcarbodiimide. The ester is coupled with the amino group under alkaline conditions in an inert, polar, organic solvent such as dimethylformamide, an ester, ether or alcohol containing up to about six carbon atoms. Any mild alkaline reagent such as alkali metal hydroxides, carbonates or bicarbonates, or alkali metal salts of lower aliphatic carboxylic acids can be employed. If the amino acid or peptide to be coupled is in the form of an ester, sodium acetate in water is the preferred alkaline reagent. If it is in the form of a free acid, sodium hydroxide is the preferred reagent. The reaction takes place at from about 15° C. to about 30° C. during a period of from about 10 to 50 hours. It is generally most economical to use a slight molar excess, e.g., up to about 20% molar excess of one of the reactants, although equimolar quantities can also be employed.

Another coupling procedure which is especially favored is the method of using the binary salt of HOBt and diisopropylethylamine (DIEA) as described in the pending patent application, Ser. No. 376,715, which is incorporated herein by reference.

It will be apparent, also, that in the course of the synthesis, it may be necessary to protect certain groups to prevent unwanted side reactions. For example, it may be necessary to protect the hydroxyl group of tyrosine, a delta or gamma carboxyl group of aspartic or glutamic acid, or the epsilon amino group of lysine so as to prevent interference by these groups in the main desired reaction. In particular, the Xmoc, DHAmoc, 9-FMFmoc, 9-(R)$_3$Si-Fmoc and many derivatives of any of these compounds are especially useful to protect reactive side chain groups of amino acids.

Protection of side chains is a common problem in peptide synthesis and many procedures are available for dealing with it. Such procedures are known to the skilled peptide chemist. In general, the known procedures are adapted for use with the protecting groups provided by this invention. (See, for example, "Protecting Groups in Organic Synthesis", by T. W. Green, John Wiley, and Sons, 1981.)

Any of the usual groups employed for protecting or blocking carboxyl groups in peptide chemistry can be employed in this instance. The principal criteria for selection of such groups, as is well known to the skilled artisan is that they should be easily placed on, stable to the reaction condition, and easily removed. Generally, the most preferred procedure is to form esters according to procedures known to one skilled in the art, and this is the preferred procedure for this reaction. The preferred esters are alkyl or alkylaryl groups containing up to eight carbon atoms such as methyl, ethyl, tert-butyl, phenyl, benzyl or p-methylbenzyl.

Further to methods of synthesizing peptides by solid phase, typical reaction apparatus useful for solid phase peptide synthesis (SPPS) are polypropylene vials or flasks which can be subjected to mixing by passage of an inert gas such as nitrogen or to vortex mixing or shaking. These flasks are often equipped with a fritted glass filter to remove excess liquid solvents and reagents by using pressure or suction filtration. Use of these types of flasks will minimize handling of the solid support(s).

Other apparatus useful for SPPS are columns packed with solid supports. Solid supports which function in SPPS are disclosed hereinabove. There are two methods in general use which employ columns. One, the Merrifield method, employs the solid support for attachment of the amino acid or peptide residues. This method employs N-protected amino acids as building blocks which are added to an amino acid or peptide residue attached to the solid support at the carbonyl (acid) end of the molecule. After the peptide bond has been formed, the protecting group is removed and the cycle repeated. When a peptide having the desired sequence has been synthesized, it is then removed from the support.

The second method, inverse Merrifield, employs reagents attached to solid supports in a series of columns. The amino acid or peptide residue is passed through these columns in series to form the desired amino acid sequence. (See U.S. Pat. No. 4,623,484 incorporated herein by reference).

CLEAVAGE OF THE PROTECTING GROUP

As mentioned herein a special advantage of one subclass of the subject compounds as blocking agents for amino acids and peptides is that these blocking agents can be cleaved under conditions which are orthogonal to those employed with Fmoc, Z or tBoc. The second class of compounds of the invention have the advantage of being more soluble than Fmoc in organic solvents commonly used for peptide synthesis, yet these compounds are cleaved under similar conditions as for Fmoc cleavage and have one of the other advantages of Fmoc, e.g. orthogonal to Z and tBoc.

The first class of compounds (orthogonal to Fmoc) require a base stronger than piperidine to effect cleavage of the protecting group. In other words, under conditions and within the time which piperidine will completely cleave Fmoc (or a group of similar reactivity) from an amino acid, the present blocking groups are not affected, i.e., they are stable and there is no danger of premature deblocking of the subject groups during a cleavage reaction to remove an Fmoc substituent from another reactive group on the same amino acid or even elsewhere on a growing peptide.

Typical bases useful in removing protecting groups which are orthogonal to Fmoc, and provided in accordance with Formula II, are in situ generated fluoride ion (inorganic fluoride ion), 1,5,9-triazabicyclo[4,4,0]-dec-5-ene (TBD), 1,8-diazabicyclo[5,4,0]undec-7-ene (DBU , 1,5-diazabicyclo 4,3,0]non-7-ene (DBN).

The second class of compounds (similar to Fmoc) can be cleaved with simple amines typically used with Fmoc. In particular, Fmoc is a base-labile, acid-stable protecting group which can readily be cleaved by simple amines like piperidine. Such ready cleavage makes these compounds especially useful as N-α-amino protecting groups since rapid deblocking time allows one to maintain shorter cycling times for addition of an amino acid to a growing peptide chain. It is preferred that the simple amine is a primary or secondary amine, with a secondary amine being most preferred, of the formula $HNR_aR_b$ wherein $R_a$ and $R_b$ are independently hydrogen, lower alkyl or substituted lower alkyl, the lower alkyl being substituted with OH, $CH_3$, or $CH_2CH_3$ or $R_a$ and $R_b$ taken together form a mono or bicyclic ring containing from 4 to 10 ring carbon atoms and 1 or 2 heteroatoms selected from the group consisting of nitrogen, sulfur or oxygen.

Typical examples of useful amines include ethanolamine, morpholine, piperidine, diethylamine, 2,6-dimethylpiperidine, piperazine, diethyl amine and ethylamine and the like. Piperidine is the most preferred amine for cleaving protecting groups similar to Fmoc.

EXAMPLES

The invention will now be illustrated by examples. The examples are not intended to be limiting of the scope of the present invention. In conjunction with the general and detailed description above, the examples provide further understanding of the present invention and outlines a synthesis of preferred embodiments of the invention.

The following examples represent preferred embodiments of the compositions of the invention and methods for carrying out the blocking and deblocking of amides as can be applied to peptide and polypeptide synthesis. The starting materials for the examples whose method of preparation are not indicated, are commercially available compounds which would be available from chemical supply houses well known to the art such as Aldrich Chemical Co.

Preparation of 9-Xanthenylmethyl derivatives

EXAMPLE 1

9-Xanthenemethanol: To a suspension of 7.5 g of lithium aluminum hydride in 360 mL of dry ether was added dropwise a solution of 30 g of xanthene-9-carboxylic acid in 90 mL of freshly distilled THF at 0° C. over a period of 30 minutes. The mixture was stirred at room temperature until the color had changed from grey to brownish red (ca. 1.5 hours) The excess $LiAlH_4$ was decomposed by the slow addition, while stirring, of a mixture of 60 mL of methanol and 25 mL of water at room temperature. The milky white suspension was filtered (sintered glass funnel) and rinsed with ether ($3\times50$ mL). The filtrate was washed with water ($2\times200$ mL), dried over anhydrous $MgSO_4$ and the solvent was evaporated under reduced pressure to give 27.5 g (100%) of the crude alcohol as an off-white solid. Recrystallization from Skelly F—ether (2:1) afforded 23.59 g (86.4%) of the pure 9-xanthenemethanol as white crystals, m.p. 66°-68° C.; IR (KBr): 3290 cm$^{-1}$ (OH); $^1$H NMR (CDCl$_3$): δ b 1.70 (t, 1H, OH), 3.71 (dt, 2H, $CH_2$), 4.09 (t, 1H, CH), 6.95-7.40 (m, 8H, aryl).

EXAMPLE 2

9-Xanthenylmethyl Carbanilate (Xmoc-aniline): To a mixture of 1.0 g of 9-xanthenemethanol and 0.51 mL of phenyl isocyanate in 5.0 mL of dry benzene was added two drops of triethylamine. The mixture was heated in an oil bath at 80° C. for 20 hours and cooled in an ice bath for 2 hours. The precipitated crystals were filtered and rinsed with Skelly B to give 1.48 g (95.2%) of the crude urethane as white crystals. Recrystallization from EtOAc—Skelly B (5:1) gave 1.37 g (88.1%) of the pure Xmoc-aniline as white needles, m.p. 180°-181° C.; IR (KBr): 3350 (NH), 1705 (C=O) cm$^{-1}$; $^1$H NMR (CDCl$_3$): δ 4.30 (m, 3H, CHCH$_2$O), 6.55 (b, 1H, NH), 6.90-7.40 (m, 13H, aryl).

Anal. Calcd for $C_{21}H_{17}NO_3$: C, 76.12; H, 5.17; N, 4.23. Found: C, 76.16; H, 5.39; N, 4.15.

EXAMPLE 3

9-Xanthenylmethyl p-Chlorocarbanilate (Xmoc-PCA): To a mixture of 2.0 g of 9-xanthenemethanol and 1.52 g of p-chlorophenyl isocyanate in 10 mL of dry benzene was added 2 drops of triethylamine. The mixture was heated in an oil bath at 80° C. for 2 hours, cooled to room temperature and treated with 10 mL of Skelly B. The precipitated crystals were removed by filtration and rinsed with Skelly B ($2\times5$ mL) to give 3.36 g (97.7%) of the crude urethane as white crystals. Recrystallization from ethyl acetate—Skelly B (2:1) gave 3.14 g (91.3%) of the pure Xmoc-PCA as white needles, m.p. 150-152° C.; IR (KBr): 3340 (NH), 1700

(C=O) cm$^{-1}$; $^1$H NMR (CDCl$_3$): δ 5 4.30 (m, 3H, CHCH$_2$O), 6.55 (b, 1H, NH), 7.00–7.40 (m, 12H, aryl).

Anal Calcd for C$_{21}$H$_{16}$NO$_3$Cl: C, 68.95; H, 4.41; N, 3.83. Found: C, 68.86; H, 4.35; N, 3.82.

EXAMPLE 4

9-Xanthenylmethyl Chloroformate (Xmoc-Cl): To an ice-cold solution of 40 mL of liquid phosgene, condensed at −78° C., in 100 mL of dry THF was added dropwise a solution of 25 g of 9-xanthenemethanol in 200 mL of dry THF over a period of 30 minutes. The mixture was stirred at room temperature for 2 hours. The excess phosgene along with the solvent was evaporated with the aid of a water aspirator in a hood to give 32.4 g (100%) of the crude chloroformate as an off-white solid. Recrystallization from Skelly F gave 31.47 g (97.3%) of the pure Xmoc-Cl as white crystals, m.p. 64°–65° C.; IR (KBr) 1770 (C=O) cm$^{-1}$; $^1$H NMR (CDCl$_3$): δ 4.40 (s, 3H, CHCH$_2$O), 7.08–7.42 (m, 8H, aryl).

Anal. Calcd for C$_{15}$H$_{11}$O$_3$Cl: C, 65.59; H, 4.04; Cl, 12.91. Found: C, 65.62; H, 4.23; Cl, 13.06.

EXAMPLE 5

9-Xanthenylmethyl Azidoformate (Xmoc-N$_3$): To an ice-cold solution of 0.4 g of sodium azide in 5 mL of distilled water was added dropwise a solution of 1.0 g of 9-xanthenylmethyl chloroformate in 5 mL of acetone over a period of 20 minutes. The mixture was stirred at room temperature for one hour, diluted with 10 mL of water, and extracted with ether (3×20 mL). The combined ether extracts were dried over MgSO$_4$, filtered, and the solvent was evaporated in vacuo to give 1.02 g (99.6%) of the crude azidoformate as an off-white oil. Crystallization from Skelly F gave 0.72 g (70.32%) of the pure Xmoc-N$_3$ as white crystals, m.p. 59°–61° C.; IR (KBr): 1720 (C=O) cm$^{-1}$; $^1$H NMR (CDCl$_3$): δ 4.22–4.38 (m, 3H, CHCH$_2$O), 7.03–7.40 (m, 8H, aryl).

Anal. Calcd for C$_{15}$H$_{11}$N$_3$O$_3$: C, 64.05; H, 3.94; N, 14.94. Found: C, 64.24; H, 3.88; N, 14.91.

EXAMPLE 6

Succinimidyl 9-Xanthenylmethyl Carbonate (Xmoc-OSu): To a solution of 7.0 g of 9-xanthenylmethyl chloroformate and 3.0 g of N-hydroxysuccinimide in 75 mL of freshly distilled THF was added dropwise 3.6 mL of triethylamine at 0° C. over a period of 20 minutes. The mixture was stirred at room temperature for 2 hours. The precipitated Et$_3$N.HCL was filtered and rinsed with THF (2×30 mL). The filtrate was evaporated under reduced pressure to give 8.93 g (100%) of the crude carbonate as an off-white solid. Recrystallization from chloroform—Skelly B (1:2) gave 8.74 g (97.9%) of the pure Xmoc-OSu as white crystals, m.p. 158°–159.5° C; IR (KBr): 1795, 1820 (C=O, carbonate), 1740 (C=O, succinimide) cm$^{-1}$; $^1$H NMR (CDCl$_3$): δ 2.80 (s, 4H, CH$_2$CH$_2$), 4.38 (m, 3h, CHCH$_2$O), 7.05–7.38 (m, 8H, aryl).

Anal. Calcd for C$_{19}$H$_{15}$NO$_6$: C, 64.57; H, 4.28; N, 3.96. Found: C, 64.43; H, 4.39; N, 3.90.

EXAMPLE 7

9-Chloromethylxanthene: To a mixture of 4.0 g of 9-xanthenemethanol and 3.0 mL of freshly distilled thionyl chloride in 30 mL of freshly distilled THF was added dropwise 1.7 mL of pyridine over a period of 15 minutes. The mixture was heated in an oil bath at 50° C. for 12 hours, cooled to room temperature, and washed with half sat'd brine (30 mL), sat'd NaHCO$_3$ (30 mL) and water (2×30 mL). The organic layer was dried over MgSO$_4$ and the solvent was evaporated in vacuo to give 4.16 g (95.7%) of the crude 9-chloromethylxanthene as an off-white solid. Recrystallization from CH$_3$OH—CH$_2$Cl$_2$(4:1) gave 3.53g (81.35%) of the pure 9-chloromethylxanthene as white needles, m.p. 104.5°–106° C.; $^1$H NMR (CDCl$_3$):δ 3.67 (d, 2H, CH$_2$), 4.32 (t, 1H, CH), 7.04–7.46 (m, 8H, aryl).

Anal. Calcd for C$_{14}$H$_{11}$OCl: C, 72.89; H, 4.81. Found: C, 72.79; H, 4.81.

EXAMPLE 8

2,7-Dichloroxanthene-9-carboxylic Acid: To a suspension of 10 g of xanthene-9-carboxylic acid and 14 g of N-chlorosuccinimide in 80 mL of acetic acid was added with stirring dropwise 2.0 mL of conc. HCl over a period of 5 minutes. The mixture was stirred at room temperature for 12 hours and quenched by the addition of 150 mL of water. The precipitated solid was removed by filtration, rinsed with water, and dried in air to give 12.6 g (100%) of the crude carboxylic acid as a white solid. Recrystallization from MeOH—EtOAc (2:1) gave 6.98 g (55.2%) of the pure 2,7-dichloroxanthene-9-carboxylic acid as colorless small needles, m.p. 273°–275° C. (dec.); IR (KBr): 2970 (b, OH), 1695 (C=O) cm$^{-1}$; $^1$H NMR (DMSO-d$_6$): δ 5.01 s, 1H, CH), 7.05–7.50 (m, 6H, aryl).

Anal. Calcd for C$_{14}$H$_8$Cl$_2$O$_3$: C, 56.98; H, 2.73. Found: C, 57.05; H, 2.74.

EXAMPLE 9

2,7-Dichloro-9-xanthenemethanol: A. From 2,7-Dichloroxanthene-9-carboxylic Acid: To a suspension of 0.75 g of LiAlH$_4$ in 90 mL of anhydrous ether was added dropwise a solution of 3.0 g of 2,7-dichloroxanthene-9-carboxylic acid in 45 mL of freshly distilled THF over a period of 25 minutes. The mixture was stirred at room temperature until the color had changed from grey to light brown (ca. 6hr). The excess LiAlH$_4$ was decomposed by the slow addition of 10 mL of methanol and 2 mL of water while stirring. The suspended precipitate was filtered, rinsed with ether (2×30 mL) and discarded. The combined filtrate was washed with water (2×40 mL), dried over MgSO$_4$, and evaporated under reduced pressure to give 1.53 g (53.6%) of the alcohol as a white solid. Recrystallization from Skelly B—EtOAc (4:1) gave 1.21 g (42.36%) of the 2,7-dichloro-9-xanthenemethanol as a white fluffy solid, m.p. 134.5°–136° C.; IR (KBr): 3250 (b, OH) cm$^{-1}$; $^1$H NMR (CDCl$_3$): δ 1.65 (b, 1H, OH), 3.75 (d, 2H, CH$_2$O), 4.01 (t, 1H, CH), 6.94–7.40 (m, 6H, aryl).

Anal. Calcd for C$_{14}$H$_{10}$O$_2$Cl$_2$: C, 59.81; H, 3.59. Found: C, 60.73; H, 3.91. B. From 9-Xanthenemethanol: To a suspension of 3.0 g of 9-xanthenemethanol and 4.2 g of N-chlorosuccinimide in 25 mL of freshly distilled THF and 12.5 mL of water was added dropwise 2.0 mL of conc. HCl over a period of 5 minutes. The mixture was stirred at room temperature for 6 hours and poured into 200 mL of water with stirring. The precipitated solid was filtered, rinsed with water (2×30 mL), and dried in air to afford 3.95 g (100%) of the crude alcohol. Recrystallization from Skelly B—EtOAc (4:1) gave 1.35 g (34%) of 2,7-dichloro-9-xanthenemethanol as a fluffy solid, m.p. 134.5°–136° C., identified by the mixture melting point, IR and NMR spectral comparison with an authentic sample obtained by the reduction of 2,7-dichloroxanthene-9-carboxylic acid.

EXAMPLE 10

2,7-Dichloro-9-xanthenylmethyl p-Chlorocarbanilate (DC-Xmoc-PCA): To a mixture of 1.0 g of 2,7-dichloro-9-xanthenemethanol and 0.57 g of p-chlorophenyl isocyanate in 10 mL of dry benzene was added one drop of triethylamine. The mixture was heated in an oil bath at 82° C. for 20 hours, cooled to room temperature, and the solvent was evaporated in vacuo to give 1.53 g (100%) of the crude urethane as an off-white solid. Recrystallization from Skelly B—ethyl acetate (2:1) gave 1.08 g (70.5%) of the pure DC-Xmoc-PCA as colorless needles, m.p. 144.5°-146.5° C.; IR (KBr): 3320 (NH), 1695 (C=O) cm$^1$H NMR (CDCl$_3$): δ 4.27 (5, 3H, CH—CH$_2$O), 6.69 (b, 1H, NH), 6.95–7.50 (m, 10H, aryl).

Anal. Calcd for $C_{21}H_{14}NO_3Cl_3$: C, 58.02; H, 3.25; N, 3.22. Found: C, 57.75; H, 3.11; N, 3.25.

EXAMPLE 11

9-Xanthenylmethyl Phenylacetate: To a mixture of 1.5 g of 9-xanthenemethanol and 0.98 g of phenylacetic acid in 20 mL of dry THF was added 1.50 g of dicyclohexylcarbodimide. The mixture was stirred at room temperature for 4 hours. The precipitated dicyclohexylurea (DCU) was removed by filtration, rinsed with ether (2×5 mL) and discarded. The filtrate was evaporated in vacuo to afford 2.35 g of a colorless oil which was chromatographed on silica gel (230–400 mesh, 4×40-cm packed column) with an eluant consisting of Skelly B—EtOAc (3:1) to give 1.92 g (82.2%) of the crude acetate as a colorless solid. Recrystallization from Skelly B gave 1.23 g 52.7%) of the pure 9-xanthenylmethylphenyl acetate as colorless needles, m.p. 77°-79° C.; IR (KBr): 1723 (C=O) cm ; $^1$H NMR (CDCl$_3$) 5 3.59 (s, 2H, CH$_2$Ar), 4.10 (s, 3H, CHCH$_2$O), 6.80–7.70 (m, 13H, aryl).

Anal. Calcd for $C_{22}H_{18}O_3$: C, 79.98; H, 5.49. Found: C, 79.90; H, 5.32.

EXAMPLE 12

9-Xanthenylmethyl Phenylcarbonate: To a mixture of 0.52 g of phenol and 1.5 g of 9-xanthenylmethyl chloroformate in 15 mL of freshly distilled THF was added dropwise at 0° C. 0.76 mL of triethylamine. The mixture was stirred at room temperature for 90 minutes. The precipitated salt, Et$_3$N.HCl, was removed by filtration, rinsed with ether (2×5 mL) and discarded. The filtrate was evaporated in vacuo to give 1.82 g (100%) of the crude carbonate. Recrystallization from Skelly B—chloroform (3:1) gave 1.57 g (86.5%) of the pure 9-xanthenylmethyl phenylcarbonate as colorless crystals, m.p. 143°-144° C., IR (KBr): 1757 (C=)) cm$^-1$; $^1$H NMR (CDCl$_3$) 5 4.38 (s, 3H, CHCH$_2$O), 6.90–7.80 (m, 13H, aryl).

Anal. Calcd for $C_{21}H_{16}O_4$: C, 75.89; H, 4.85. Found: C, 75.90; H, 4.93.

Preparation of 9,10-Dihydro-9-anthracenylmethyl derivatives

EXAMPLE 13

1. 9,10-Dihydroanthracene-9-carboxylic Acid: To a solution of 10 g of 9,10-dihydroanthracene in 40 mL of freshly distilled THF and 160 mL of dry ether was added dropwise 42 mL of 1.35M n-butyllithium. The mixture was refluxed for 20 hours, cooled to −78° C., and poured jet-wise onto 15 g of crushed dry-ice. The mixture was stirred while being warmed gradually to room temperature and quenched with 100 mL of water. The organic layer which separated was extracted with 2% KOH (3×70 mL). The combined aqueous layer was neutralized with conc. HCl (Congo Red). The precipitate was filtered, rinsed with water (2×10 mL), and dried in air to afford 12.0 g (100%) of the crude carboxylic acid as a white solid. Recrystallization from methanol gave 8.82 g (73.1%) of the pure 9,10-dihydroanthracene-9-carboxylic acid as white needles, m.p. 207°-209° C.; IR (KBr): 3020 (b, OH), 1705 (C=O) cm$^-1$; $^1$H NMR (DMSO-d$_6$): δ 4.02 (dd, 2H, CH$_2$), 5.00 (s, 1H, CH), 7.00–7.50 (m, 8H, aryl).

2. 9,10-Dihydro-9-anthracenemethanol: To a suspension of 3.0 g of LiAlH$_4$ in 100 mL of dry ether was added dropwise at 0° C. a solution of 9.0 g of 9,10-dihydroanthracene-9-carboxylic acid in 50 mL of freshly distilled THF over a period of 30 minutes. The mixture was stirred at room temperature until the color had changed from grey to greenish (approx. 1 hour). The mixture was cooled in an ice bath and the excess LiAlH$_4$ was decomposed by the slow addition of 12 mL of methanol and 6 mL of water. The precipitated solid was removed by filtration and rinsed with ether (2×40 mL). The filtrate was dried over MgSO$_4$ and the solvent was evaporated under reduced pressure to give 8.44 g (100%) of the crude alcohol as an off-white solid. Recrystallization from Skelly B—ether (3:1) gave 7.08 g (83.9%) of the pure 9,10-dihydro-9-anthracenemethanol as white needles, m.p. 83°-85° C.; IR (KBr): 3340 (OH) cm$^-1$; $^1$H NMR (CDCl$_3$): 1.58 (b, 1H, OH), 3.69 (d, 2H, CH$_2$O), 4.05 (dd, 2H, ArCH$_2$Ar), 4.17 (t, 1H, CH), 7.15–7.50 (m, 8H, aryl).

EXAMPLE 14

3,10-Dihydro-9-anthracenylmethyl p-Chlorocarbanilate (DHAmoc-PCA): To a mixture of 0.8 g of 9,10-dihydro-9-anthracenemethanol and 0.6 g of p-chlorophenyl isocyanate in 5.0 mL of dry benzene was added 1 drop of thiethylamine. The mixture was heated in an oil bath at 84° C. for 3 hours, cooled to room temperature, and the solvent was evaporated in vacuo to give an oil which was triturated with Skelly B to give 1.42 g (100%) of the crude urethane as an off-white solid. Recrystallization rom Skelly B—EtOAc (4:1) gave 1.18 g (85.25%) of the pure DHAmoc-PCA as white needles, m.p. 134°-136° C.; IR (KBr): 3285 (NH), 1700 (C=O) cm$^-1$; $^1$NMR (CDCl$_3$): δ 4.09 (dd, 2H, ArCH$_2$Ar), 4.26 (d, 2H, CH$_2$O), 4.39 (t, 1H, CH), 6.58 (b, 1H, NH), 7.15–7.50 (m, 12H, aryl).

Anal. Calcd for $C_{22}H_{18}NO_2Cl$: C, 72.62; H, 4.99; N, 3,85. Found: C, 72.35; H, 4.86; N, 3.84.

Preparation of Substituted Fmoc Derivatives

A. Substitutions at position 9

EXAMPLE 15

9-Trimethylsilylfluorene: To a solution of 20 g (0.12 moL) of fluorene in 400 mL of dry ether was added dropwise 90 mL of 1.4M n-butyllithium at room temperature. The mixture was refluxed for 3 hours, cooled in an ice bath, and treated with 18 mL (0.14 moL) of freshly distilled chlorotrimethylsilane in one portion. The mixture was refluxed for 3 hours, cooled to room temperature, and washed with sat'd NaHCO$_3$ (2×100 mL) and water (100 mL). The pooled aqueous layer was extracted with ether (2×100 mL). The combined organic extracts were dried over anhydrous MgSO$_4$ and the solvent was evaporated in vacuo to afford 27.5 g (95.8%) of crude silane as an off-white solid. Recrystallization from 95% ethanol gave 20.8 g (72.5%) of the pure trimethylsilylfluorene as white needles, m.p. 98°–99° C.; $^1$H NMR (CDCl$_3$): δ -0.04 (s, 9H, SiMe$_3$), 3.90 (s, 1H, CH), 7.10–8.00 (m, 8H, aryl).

EXAMPLE 16

1. Chloromethyl Benzyl Ether: Dry hydrogen chloride gas, made by dropwise addition of 1000 mL of conc. hydrochloric acid to 1000 mL of conc. sulfuric acid, was passed through a mixture of 130 mL of benzyl alcohol and 100 mL of 37% aqueous formaldehyde at 10° C. until saturation (ca. 8 hr). The mixture was stirred at room temperature for 2 hours and transferred to a separatory funnel. The bottom layer was discarded while the top layer was dried over anhydrous calcium chloride. The excess hydrogen chloride was removed by stirring under vacuo with the aid of a water aspirator to give 188 g (95.4%) of the crude chloromethyl benzyl ether. Distillation gave 138 g (69.8%) of the pure benzyl ether as a colorless liquid, b.p. 46°–48° C. (0.5 mmHg). $^1$H NMR (CDCl$_3$) δ 4.73 (s, 2H, CH$_2$Ar), 5.51 (s, 2H, CH$_2$Ar), 5.51 s, 2H, CH$_2$Cl), 7.38 (s, 5H, Ar).

2. 9-Trimethylsilyl-9-fluorenemethanol: To a solution of 10 g of 9-trimethylsilylfluorene in 100 mL of dry ether was added dropwise 30.5 mL of 1.4M n-butyllithium. The mixture was refluxed for 3 hours, cooled in an ice bath, and treated with 6 mL of freshly distilled chloromethyl benzyl ether. The mixture was stirred at room temperature for 30 minutes, quenched with water (10 mL) and washed with water (2×50 mL). The pooled aqueous layer was extracted with ether (2×50 mL). The combined organic extracts were dried over MgSO$_4$, and the solvent was evaporated under reduced pressure to give a yellow oil which was dissolved in 120 mL of 100% ethanol and treated with 2.0 g of 5% palladium on charcoal at 0° C. The mixture was stirred under a hydrogen atmosphere at 45° C. for 20 hours. The catalyst was filtered and rinsed with ethanol (2×10 mL). The filtrate was evaporated in vacuo to afford 8.96 g of oil which was chromatographed on silica gel (230–400 mesh, 3.5×45-cm packed column) with an eluant of Skelly B—ether (3:1), to give 5.48 g (48.7%) of colorless oil. Crystallization from Skelly B gave 5.09 g (45.2%) of pure alcohol as colorless crystals, m.p. 105°–106° C.; IR (KBr): 3380 cm$^{-1}$ (b, OH); $^1$H NMR (CDCl$_3$): δ -0.12 (s, 9H, SiMe$_3$), 1.20 (b, 1H, OH), 4.47 (s, 2H, CH$_2$), 7.05–8.00 (m, 8H, aryl).

Anal. Calcd for C$_{17}$H$_{20}$OSi: C, 76.07; H, 7.51. Found: C, 76.13; H, 7.60.

EXAMPLE 17

9-Trimethylsilyl-9-fluorenylmethyl p-Chlorocarbanilate (TMS-Fmoc-PCA): A mixture of 3.0 g of 9-trimethylsilyl-9-fluorenemethanol and 1.72 g of p-chlorophenyl isocyanate in 8 mL of dry benzene was heated in an oil bath at 80° C. for 4 hours. The mixture was cooled to room temperature and treated with 50 mL of Skelly F with stirring. The precipitate was removed by filtration, washed with Skelly F, and recrystallized from Skelly B to afford 4.1 g (86.9%) of the urethane as colorless needles, m.p. 126°–127° C.; IR (KBr): 3290 NH), 1700 (C=O) cm$^{-1}$; $^1$H NMR (CDCl$_3$): δ -0.12 (s, 9H, SiMe$_3$), 5.10 (s, 2H, CH$_2$), 6.21 (b, 1H, NH), 6.90–8.00 (m, 12H, aryl).

Anal. Calcd for Si: C$_{24}$H$_{24}$NO$_2$ClSi: C, 68.31; H, 5.73; N, 3.32. Found: C, 68.35; H, 5.74; N, 3.35.

EXAMPLE 18

2,7-Bis(trimethylsilyl)-9-fluorenylmethyl Carbanilate (BTS-Fmoc-aniline): A mixture of 0.71 g of 2,7-bis(trimethylsilyl)fluorene-9-methanol and 0.22 mL of phenyl isocyanate in 4 mL of dry benzene was heated in an oil bath at 80° C. for 8 hours. The mixture was cooled to room temperature and treated with 20 mL of Skelly B. The precipitate was removed by filtration, washed with Skelly B, and recrystallized from Skelly B—EtOAc (5:1) to give 0.81 g (87.13%) of the urethane as white crystals, m.p. 178°–179° C.; IR (KBr): 3240 (NH), 1710 (C=O) cm$^{-1}$; $^1$H NMR (CDCl$_3$): δ 1.31 (s, 18H, SiMe$_3$), 4.30 (t, 1H, CH), 4.58 (d, 2H, CH$_2$), 6.61 (b, 1H, NH), 6.90–7.90 (m, 11H, aryl).

Anal. Calcd for C$_{27}$H$_{33}$NO$_2$Si$_2$: C, 70.54; H, 7.24; N, 3.05. Found: C, 70.40; H, 7.01; N, 2.92.

EXAMPLE 19

9-Trimethylsilyl-9-fluorenylmethyl Carbanilate (TMS-Fmoc-aniline): A mixture of 1.0 g of 9-trimethylsilyl-9-fluorenemethanol and 0.4 mL of phenyl isocyanate in 2.0 mL of dry benzene was heated in an oil bath at 80° C. for seven hours. The mixture was cooled to room temperature and triturated with 20 mL of Skelly F. The crystals deposited were removed by filtration, rinsed with Skelly F, and recrystallized from Skelly B to give 1.31 g (91.9%) of the urethane as white crystals, m.p. 137°–138° C.; IR(KBr): 3300 (NH), 1700 (C=O) cm$^{-1}$; $^1$H NMR (CDCl$_3$) δ -0.12 (s, 9H, SiMe$_3$), 5.07 (s, 2H, CH$_2$), 6.21 (b, 1H, NH), 6.80–8.00 (m, 13H, aryl).

Anal. Calcd for C$_{24}$H$_{25}$NO$_2$Si: C, 74.38, H, 6.50, N, 3.61. Found: C, 74.12; H, 6.40; N, 3.52.

EXAMPLE 20

9-Trimethylsilyl-9-fluorenylmethyl Chloroformate: To a solution of 1.5 mL of phosgene, condensed at -78° C., in 10 mL of freshly distilled THF was added dropwise a solution of 2.0 g of 9-trimethylsilyl-9-fluorenemethanol in 20 mL of freshly distilled THF at 0° C. over a period of 30 minutes. The mixture was stirred at 0° C. for 30 minutes and warmed to room temperature. The excess phosgene along with the THF was removed by a water aspirator in a hood to afford an oil which was triturated with Skelly B to give 2.39 g (96.9%) of the crude chloroformate as an off-white solid. Recrystallization from Skelly B gave 2.15 g (87.2%) of the pure chloroformate as colorless crystals, m.p. 78°–79° C. (dec.); IR (KBr): 1770 cm$^{-1}$ (C=O); $^1$H NMR (CDCl$_3$): δ -0.11 (s, 9H, SiMe$_3$), 5.03 (s, 2H, CH$_2$O), 730.7.95 (m, 8H, aryl).

Anal. Calcd for C$_{18}$H$_{19}$SiO$_2$Cl: C, 65.34; H, 5.74. Found: C, 65.50; H, 5.60.

EXAMPLE 21

9-Triphenylsilylfluorene: To a solution of 17 g of fluorene (102.4 mmol) in 300 mL of dry ether was added 46 mL of 2.3M n-butyllithium dropwise over a period of 20 minutes. The mixture was refluxed for 3 hours, cooled in an ice bath, and treated in one portion with a solution of 24 g (81.46 mmol) of triphenylsilyl chloride in 100 mL of dry benzene. The mixture was refluxed for 24 hours, cooled to room temperature, and washed with sat'd NH$_4$Cl (100 mL), brine (150 mL), and water (150 mL). The organic layer was dried over MgSO$_4$ and the solvent was evaporated in vacuo to give a yellow residue which was triturated with methanol to afford 34.18 g (98.9%) of the crude silane as an off-white solid. Recrystallization from EtOAc—EtOH (4:1) gave 27.46 g (79.5%) of the pure triphenylsilane as white needles, m.p. 182°-193° C.; $^1$H NMR (CDCl$_3$): δ 4.72 (s, 1H, CH), 6.82-7.90 (m, 23H, aryl).

EXAMPLE 22

9-Diphenyl(methyl)silylfluorene: To a solution of 5.5 g (33.13 mmol) of fluorene in 130 mL of dry ether was added dropwise 15 mL of 2.3M n-butyllithium. The mixture was refluxed for 3 hours, cooled to 0° C., and treated with 4.8 mL (23.26 mmol) of diphenyl(methyl)-silyl chloride in one portion. The mixture was refluxed for 21 hours, cooled to room temperature, diluted with 100 mL of ethyl acetate, and washed with half sat'd NH$_4$Cl (100 mL) and water (2×100 mL). The organic layer was dried over anhydrous MgSO$_4$ and the solvent was evaporated in vacuo to give an oil which was triturated with methanol to give 8.16 g (96.54%) of the crude silane as a yellow solid. Recrystallization from EtOAc—EtOH (1:1) gave 7.27 g (86.01%) of the pure 9-diphenyl(methyl)silylfluorene as white crystals m.p. 163°-165° C.; $^1$H NMR (CDCl$_3$): δ 0.15 (s, 3H, SiCH$_3$), 4.45 (s, 1H, CH), 6.75-8.00 (m, 18H, aryl).

Anal. Calcd for C$_{26}$H$_{22}$Si: C, 86.14; H, 6.12. Found: C, 86.21, H, 6.26.

EXAMPLE 23

9-Dimethyl(phenyl)silylfluorene: To a solution of 5.0 g (30.1 mmol) of fluorene in 100 mL of dry ether was added dripwose 24 mL of 1.4M n-butyllithium over a period of 20 minutes. The mixture was refluxed for three hours, cooled in an ice bath, and treated with 4.8 mL (29.0 mmol) of dimethyl(phenyl)silyl chloride in one portion. The mixture was refluxed for 2 hours, cooled to room temperature, and washed with sat'd NH$_4$Cl (50 mL) and water 50 mL). The pooled aqueous layer was extracted with ether (2×50 mL). The combined organic extracts were dried over MgSO$_4$, and the solvent was evaporated in vacuo to afford 8.70 g (100%) of the crude silane as an off-white solid. Recrystallization from 95% ethanol gave 6.32 g (72.6%) of the pure 9-dimethyl(phenyl)silylfluorene as white needles, m.p. 86.5°-87.5° C.; $^1$H NMR (CDCl$_3$): δ 0.10 (s, 6H, SiMe$_2$), 4.09 (s, 1H, CH), 6.95-8.00 (m, 13H, aryl).

Anal. Calcd for C$_{21}$H$_{20}$Si: C, 83.94; H, 6.71. Found: C, 83.82; H, 6.64.

EXAMPLE 24

9-Triisopropylsilylfluorene: To a solution of 3.0 g (18.07 mmol) of fluorene in 50 mL of dry ether and 25 mL of freshly distilled THF was added dropwise 13 mL of 1.4M n-butyllithium. The mixture was refluxed for 3 hours, cooled to room temperature, and treated with 3 mL (14.02 mmol) of triisopropylsilyl chloride in one portion. The mixture was refluxed for 3 days, cooled to room temperature, and washed with sat'd NH$_4$Cl (2×50 mL) and water (50 mL). The organic layer was dried over MgSO$_4$ and the solvent was evaporated in vacuo to give an oil which was triturated with methanol to afford 3.34 g (73.8%) of the crude silane as a yellowish solid. Recrystallization from EtOH gave 2.98 g (65.9%) of 9-triisopropylsilylfluorene as white needles, m.p. 122°-123° C.; $^1$H NMR (CDCl$_3$): δ 0.91 (d, 18H, Si-C-Me$_2$), 1.09-1.42 (hept, 3H, Si-CH-Me$_2$, 4.26 s, 1H, ArCHAr), 7.05-8.00 (m, 8H, aryl).

Anal. Calcd for C$_{22}$H$_{30}$Si: C, 81.92; H, 9.37. Found: C, 82.00; H, 9.15.

EXAMPLE 25

9-Dimethyl(phenyl)silyl-9-fluorenylmethyl Benzyl Ether: To a solution of 2.0 g of 9-dimethyl(phenyl)silyl-fluorene in 40 mL of dry ether was added dropwise 4.8 mL of 1.45M n-butyllithium. The mixture was refluxed for five hours, cooled in an ice bath and treated with 1.0 mL of freshly distilled benzyl chloromethyl ether in one portion. The mixture was stirred at 0° C. for 30 minutes and room temperature for another 30 minutes. After the addition of 20 mL of sat'd NH$_4$Cl, the organic layer was washed with water (20 mL), and the aqueous layer was extracted with ether (2×20 mL). The combined ether layers were dried over MgSO$_4$ and the solvent was evaporated in vacuo to give 2.80 g (100%) of the crude benzyl ether. Recrystallization from EtOH—EtOAc (4:1) gave 1.97 g (70.33%) of the pure 9-dimethyl(-phenyl)silyl-9-fluorenylmethyl benzyl ether as colorless crystals, m.p. 101°-103° C.; $^1$H NMR (CDCL$_3$ 5 0.08 (s, 6H, SiMe$_2$), 4.01 (s, 2H, C-CH$_2$O), 4.57 (s, 2H, O—CH$_2$Ar), 7.10-7.95 (m, 18H, aryl).

Anal. Calcd for C$_{29}$H$_{28}$SiO: C, 82.81; H, 6.71. Found: C, 82.65; H, 6.78.

EXAMPLE 26

9-Diphenyl(methyl)silyl-9-fluorenylmethyl Benzyl Ether: To a solution of 4.0 g of 9-diphenyl(methyl)silyl-fluorene in 40 mL of freshly distilled THF and 80 mL of dry ether was added dropwise 5.0 mL of 2.3M n-butyllithium. The mixture was refluxed for four hours, cooled in an ice bath, and treated with 1.5 ml of freshly distilled benzyl chloromethyl ether. The mixture was stirred at 0° C. for 30 minutes and room temperature for 3 hours. After the addition of 50 mL of half sat'd NH$_4$Cl, the organic layer was extracted with water (50 mL), and the pooled aqueous layer was extracted with ether (2×50 mL). The combined organic extracts were dried over anhydrous MgSO$_4$ and the solvent was evaporated under reduced pressure to give 5.56 g (100%) of a yellow oil which was chromatographed on silica gel (230-400 mesh, 4×45-cm packed column) with an eluant consisting of Skelly B—CH$_2$Cl$_2$(2:1), to afford 4.38 g (64.9%) of the benzyl ether as a colorless oil. Crystallization from EtOH—EtOAc (4:1) gave 3.38 g (64.9%) of the pure benzyl ether as white crystals, m.p. 103°-104° C.; $^1$H NMR (CDCl$_3$): δ 0.35 (s, 2H, SiCH$_3$), 4.02 (s, 2H, C—CH$_2$O), 4.52 (s, 2H, OCH$_2$Ar), 7.05-7.85 (m, 23H, aryl).

Anal. Calcd for C$_{34}$H$_{30}$SiO: C, 84.60; H, 6.26. Found C, 84.43; H, 6.45.

EXAMPLE 27

9-Triphenylsilyl-9-fluorenylmethyl Benzyl Ether: To a solution of 5.0 g of 9-triphenylsilylfluorene in 80 mL of dry ether and 40 mL of freshly distilled THF was added dropwise 8.5 mL of 1.55M n-butyllithium. The mixture was refluxed for 8 hours, cooled to room temperature, and treated with 1.8 mL of freshly distilled benzyl chloromethyl ether. The resulting mixture was stirred at room temperature for 10 hours and washed with half sat'd NH$_4$Cl (40 mL) and water (50 mL). The combined organic extracts were dried over MgSO$_4$ and the solvent was evaporated under reduced pressure to give 6.4 g (100%) of the crude benzyl ether as a yellow solid. Recrystallization from EtOH—EtOAc (1:1) afforded 4.47 g (69.7%) of the 9-triphenylsilyl-9-fluorenylmethyl benzyl ether as colorless crystals, m.p. 160°-161.5° C.; $^1$H NMR (CDCl$_3$): δ 4.03 s, 2H, C—CH$_2$O), 4.47 (s, 2H, ArCH$_2$O), 7.02-7.85 (m, 28H, aryl).

Anal. Calcd for C$_{39}$H$_{32}$SiO: C, 85.99; H, 5.92. Found C, 85.77; H, 5.81.

EXAMPLE 28

9-Dimethyl(phenyl)silyl-9-fluorenemethanol: To a solution of 1.0 g of 9-dimethyl(phenyl)silyl-9-fluorenylmethyl benzyl ether in 30 mL of freshly distilled THF and 10 mL of 100% ethanol was added 0.3 g of 5% palladium on charcoal. The heterogeneous mixture was shaken under hydrogen at a pressure of 45 psi in a Parr apparatus for 48 hours. The catalyst was removed by filtration and the filtrate was evaporated in vacuo to give 0.75 g (95.4%) of a colorless oil which was chromatographed on silica gel (130-400 mesh, 2×40-cm packed column) with an eluant consisting of Skelly B—ether (3:1), to afford 0.50 g (63.6%) of the pure alcohol as a colorless oil, which failed to crystallize and therefore was used directly for conversion to the corresponding carbanilates.

EXAMPLE 29

9-Dimethyl(phenyl)silyl-9-fluorenylmethyl p-Chlorocarbanilate (DMPS-Fmoc-PCA): A mixture of 0.65 g of oily 9-dimethyl(phenyl)silyl-9-fluorenemethanol and 0.3 g of p-chlorophenyl isocyanate in 3.0 mL of dry benzene was heated in an oil bath at 80° C. for 16 hours. The solvent was evaporated under reduced pressure to afford 0.95 g (100%) of a yellow oil which was chromatographed on silica gel (230-400 mesh, 2×40-cm packed column) with an eluant consisting of Skelly B—ether (3:1 , to give 0.76 g (80.6%) of the crude urethane as a white solid. Recrystallization from Skelly B gave 0.63 g (66.8%) of the pure DMPS-Fmoc-PCA as colorless crystals, m.p. 128°-129° C.; IR (KBr); 3285 cm$^{-1}$; $^1$H NMR (CDCl$_3$): δ 0.09 (s, 6H, SiMe$_3$), 5.05 (s, 2H, CH$_2$), 6.16 (b, 1H, NH), 6.80-7.90 (m, 17H, aryl).

Anal. Calcd for C$_{29}$H$_{26}$NO$_2$SiCl: C, 71.96; H, 5.41; N, 2.89. Found: C, 72.10; H, 5.38;

EXAMPLE 30

9-Dimethyl(phenyl)silyl-9-fluorenylmethyl Carbanilate (DMPS-Fmoc-aniline): A mixture of 0.32 mL of phenyl isocyanate and 1.0 g 9-dimethyl(phenyl)silyl-9-fluorenemethanol in 7.0 mL of dry benzene was heated in an oil bath at 82° C. for 20 hours. The mixture was cooled to room temperature and the solvent was evaporated in vacuo to give 1.32 g (100%) of the crude urethane as an off-white solid. Recrystallization from Skelly B gave 1.13 g (85.4%) of the pure DMPS-Fmoc-aniline as white crystals, m.p. 121°-122° C.; IR (KBr): 3380 (NH), 1730 (C=O) cm$^{-1}$; $^1$H NMR (CDCl$_3$): δ 0.10 (s, 6H, SiMe$_2$, 5.07 (s, 2H, CH$_2$), 6.18 (b, 1H, NH), 6.80-8.00 (m, 18H, aryl).

Anal. Calcd for C$_{29}$H$_{27}$NO$_2$Si: C, 77.47; H, 6.05; N, 3.12. Found: C, 77.39; H, 5.95; N, 3.13.

EXAMPLE 31

9-Diphenyl(methyl)silyl-9-fluorenemethanol: To a solution of 1.0 g of 9-diphenyl(methyl)silyl-9-fluorenylmethyl benzyl ether in 30 mL of ethyl acetate and 50 mL 100% ethanol were added 0.2 g of 5% palladium on charcoal and 0.2 g of palladium acetate. The mixture was shaken in a Parr apparatus under hydrogen at a pressure of 45 psi for 20 hours. The catalysts were filtered and rinsed with EtOAc (2×5 mL). The filtrate was evaporated in vacuo to give a yellow oil which was chromatographed on silica gel (230-400 mesh, 2×40-cm packed column) with an eluant consisting of Skelly B—ether (3:1), to give 0.24 g (29.5%) of the alcohol as a white solid. Recrystallization from Skelly B gave 0.15 g g (18.43%) of the pure alcohol as white crystals, m.p. 114°-116° C.; IR (KBr): 3540, 3450 cm$^{-1}$ (OH); $^1$H NMR (CDCl$_3$): δ 0.39 (s, 3H, SiMe$_3$), 1.57 (b, 1H, OH), 4.61 (s, 2H, CH$_2$), 6.90-7.90 (m, 18H, aryl).

Anal. Calcd for C$_{27}$H$_{24}$OSi: C, 82.61; H, 6.16. Found: C, 82.54; H, 6.21.

EXAMPLE 32

9-Diphenyl(methyl)silyl-9-fluoroenylmethyl Carbanilate (DMPS-Fmoc-aniline): A mixture of 27.3 μl of phenyl isocyanate and 0.10 g of 9-diphenyl(methyl)silyl-9-fluorenemethanol in 1.0 mL of dry benzene was heated in an oil bath at 80° C. for 16 hours. The mixture was cooled to room temperature, and the solvent was evaporated under reduced pressure to give 0.13 g (100%) of the crude urethane as a yellow oil which was chromatographed on silica gel (230-400 mesh, 2×30-cm packed column) with an eluant consisting of Skelly B—ether (3:1), to give 0.12 g (93.3%) of the urethane as a white solid. Recrystallization from Skelly B—ethyl acetate (4:1) gave 0.102 g (79.3%) of the pure DMPS-Fmoc-aniline as white needles, m.p. 159°-160° C.; IR (KBr): 3380 (NH), 1730 (C=O) cm$^{-1}$; $^1$H NMR (CDCl$_3$): δ 0.28 (s, 3H, SiCH$_3$), 5.13 (s, 2H, CH$_2$), 6.11 (b, 1H, NH), 6.80-7.90 (m, 23H, aryl).

Anal. Calcd for C$_{34}$H$_{29}$NO$_2$Si: C, 79.81; H, 5.71; N, 2.74. Found: C, 79.88; H, 5.81; N, 2.90.

EXAMPLE 33

9-Triisopropylsilyl-9-fluorenemethanol: To a solution of 1.0 g of 9-triisopropylsilylfluorene in 10 mL of dry ether and 30 mL of dry hexane was added dropwise 2.5 mL of 1.5M n-butyllithium. The mixture was refluxed for 15 hours and cooled in an ice bath. Gaseous formaldehyde, generated by heating dried paraformaldehyde at 170° C., was passed through a 8-mm tube into the reaction mixture with the aid of a slow stream of nitrogen until the deep red color had faded to pale yellow (ca. 5 min). The mixture was quenched immediately with 40 mL of half sat'd NH$_4$Cl and washed with brine (10 mL) and water (20 mL). The pooled aqueous layer was extracted with ether (2×20 mL). The combined organic extracts were dried over MgSO$_4$ and the solvent was evaporated in vacuo to give an oil which was chromatographed on silica gel (230-400 mesh, 2×40-cm packed column) with an eluant consisting of Skelly B—ether (3:1), to afford 0.63 g (57.7%) of the alcohol as a white solid. Recrystallization from Skelly F gave 0.38 g (34.8%) of the pure 9-triisopropylsilyl-9-fluorenemethanol as colorless crystals m.p. 106°-107.5° C.; IR (KBr): 3505, 3405 cm$^{-1}$ (OH); $^1$H NMR (CDCl$_3$): δ 0.83 (d, 18H, Si-C-Me$_2$), 1.20-1.42 (hept, 3H, C—S—CH), 4.71 (s, 2H, CH$_2$), 7.20-7.95 (m, 8H, aryl).

Anal. Calcd for C$_{23}$H$_{32}$SiO: C, 78.35; H, 9.15. Found: C, 78.26; H, 9.05.

EXAMPLE 34

9-Triisopropylsilyl-9-fluorenylmethyl Carbanilate (TIPS-Fmoc-analine): To a mixture of 1.0 g of 9-triisopropylsilyl-9-fluorenemethanol and 0.3 mL of phenyl isocyanate in 10 mL of dry benzene was added 2 drops of triethylamine. The mixture was heated in an oil bath at 82° C. for one hour and cooled to room temperature. The solvent was evaporated in vacuo to give 1.30 g (100%) of the crude urethane as a yellow solid. Recrystallization from Skelly B gave 1.12 g (86.02%) of the pure urethane as colorless crystals, m.p. 152.5°–154° C.; IR (KBr): 3240 (NH), 1690 (C=O) cm$^{-1}$; $^1$H NMR (CDCl$_3$); δ 0.87 (d, 18H, Si-C-Me$_2$), 1.18–1.44 (hept, 3H, C-Si-CH), 5.33 (s, 2H, CH$_2$), 6.02 (b, 1H, NH), 6.70–7.95 (m, 13H, aryl).

Anal. Calcd for C$_{30}$H$_{37}$NO$_2$Si: C, 76.39; H, 7.91; N, 2.97. Found: C, 76.27; H, 7.77; N, 2.92.

B. Substitutions of positions 2 and 7

EXAMPLE 35

9,9-Bis(trimethylsilyl)fluorene: To a solution of 10 g (42.0 mmol) of 9-trimethylsilylfluorene in 150 mL of dry ether was added dropwise 30 mL of 1.4 M n-butyllithium at room temperature over a period of 20 minutes. The mixture 0 was refluxed for 3 hours, cooled to 0° C., and treated dropwise with 6.0 mL (47.3 mmol) of freshly distilled chlorotrimethylsilane over a period of 20 minutes. The resulting mixture was refluxed for 7 hours, cooled to room temperature, and washed with sat'd sodium bicarbonate (2×100 mL) and water (100 mL). The aqueous layer was extracted with ether (2×100 mL). The combined organic extracts were dried over anhydrous MgSO$_4$ and the solvent was evaporated under reduced pressure to afford 12.9 g (99.0%) of the crude disilane as an off-white solid. Recrystallization from 95% ethanol gave 9.90 g (76.0%) of the pure 9,9-bis(trimethylsilyl)fluorene as white needles, m.p. 110°–112° C.; $^1$H NMR (CDCl$_3$): δ −0.08 (s, 18H, SiMe$_3$), 7.15–8.10 (m, 8H, aryl.).

EXAMPLE 36

2,7-Dibromo-9,9-bis(trimethylsilyl)fluorene: To a suspension of 4.0 g of 9,9-bis(trimethylsilyl)fluorene and 5.0 g of N-bromosuccinimide in 90 mL of glacial acetic acid was added 1 mL of 48% hydrobromic acid over a period of 3 minutes. The reactants dissolved as a new solid separated. After six hours, 200 mL of water was added slowly and the solid was filtered, rinsed with water, and dried in air to afford 6.04 (99.6%) of the crude dibromide as a yellowish solid. Recrystallization from acetone gave 4.51 g (74.4%) of the 2,7-dibromo-9,9-bis(trimethylsilyl)fluorene as pure white needles, m.p. 200°–201° C.; $^1$H NMR (CDCl$_3$) 5 –0.07 (s, 18H, SiMe$_3$), 7.20–7.90 (m, 6H, aryl).

Anal. Calcd for C$_{19}$H$_{24}$Br$_2$Si$_2$: C, 48.75; H, 5.16. Found: C, 49.22; H, 5.23.

EXAMPLE 37

2,7,9,9-Tetrakis(trimethylsilyl)fluorene: A mixture of 4.0 g of 2,7-dibromo-9,9-bis(trimethylsilyl)fluorene and 4.0 mL of freshly distilled chlorotrimethylsilyl)fluorene and 4.0 mL of freshly distilled chlorotrimethylsilane in 70 mL of toluene was added slowly to molten sodium (1 g of finely cut sodium in 40 mL of boiling toluene). The mixture was refluxed for 12 hours and cooled in an ice bath. Ice chips were added slowly to destroy the excess sodium. The mixture was then washed with water (2× 70 mL) and the pooled aqueous layer was extracted with ether (2×100 mL). The combined organic extracts were dried over anhydrous MgSO$_4$, and the solvent was evaporated in vacuo to give 3.63 g (93.6%) of the crude tetrasilane as an off-white solid. Recrystallization from methanol afforded 2.75 g (70.9%) of the pure 2,7,9,9-tetrakis(trimethylsilyl)fluorene $^1$H NMR (CDCl$_3$) 5 –0.10 (s, as white needles, m.p. 141°–142° C.; $^1$H NMR (CDCl$_3$): δ −0.10 (s, 18H, Me$_3$-Si-C-SiMe$_3$), 0.32 (s, 18H, Ar-SiMe$_3$), 7.20–8.00 (m, 6H, aryl).

Anal. Calcd for C$_{25}$H$_{42}$Si$_4$: C, 66.00; H, 9.31. Found: C, 66.04; H, 9.21.

EXAMPLE 38

2,7-Bis(trimethylsilyl)fluorene: To a suspension of 0.5 g of 2,7,9,9-tetrakis(trimethylsilyl)-fluorene in 15 mL of 95% ethanol was added 1.5 mL of 10% KOH. The mixture was refluxed for 2 hours and cooled in an ice bath for one hour. The precipitated crystals were removed by filtration, rinsed with water (2×5 mL), dried in air, and recrystallized from methanol to give 0.32 g (93.8%) of pure 2,7-bis(trimethylsilyl)fluorene as colorless crystals, m.p. 117°–118° C.; $^1$H NMR (CDCl$_3$): δ 0.31 (s, 18H, SiMe$_3$), 3.90 (s, 2H, CH$_2$), 7.20–7.90 (m, 6H, aryl).

Anal. Calcd for C$_{19}$H$_{26}$Si$_2$: C, 73.48; H, 8.44. Found: C, 73.23; H, 8.43.

EXAMPLE 39

2,7-Bis(trimethylsilyl)fluorene-9-methanol: To an ice-cold solution of 6.0 g of 2,7-bis(trimethylsilyl)fluorene in 100 mL of dry ether was added dropwise 18 mL of 1.3 M n-buthyllithium at 0° C. The mixture was stirred at room temperature for 30 minutes and cooled in an ice bath. Gaseous formaldehyde, generated by heating 2.5 g of dried paraformaldehyde at 170° C., was passed through a 8-mm tube into the reaction mixture with the aid of a slow stream of nitrogen until the black color had disappeared. The mixture was washed with half sat'd NH$_4$Cl (50 mL) and water (50 ml).

The pooled aqueous layer was extracted with ether (2×50 mL) and the combined organic extracts were dried over MgSO$_4$. After removal of the solvent under reduced pressure, the residue was chromatographed on silica gel (230–400 mesh, 5×60-cm packed column) with an eluant of Skelly B—ether (3:1), to afford 3.73 g (56.7%) of the alcohol as a white solid. Recrystallization from Skelly B gave 3.30 g (50.16%) of the pure alcohol as colorless crystals, m.p. 112.5°–113° C.; IR (KBr): 3250 cm$^{-1}$ (b,OH); $^1$H NMR (CDCl$_3$): δ 0.32 (s, 18H, SiMe$_3$), 1.57 (b, 1H, OH), 4.03–4.17 (m, 3H, CHCH$_2$O), 7.20–7.90 (m. 6H, aryl).

Anal Calcd for C$_{20}$H$_{28}$Si$_2$O: C, 70.53; H, 8.29. Found: C, 70.44; H, 8.26.

EXAMPLE 40

2,7-Bis(trimethylsilyl)-9-fluorenylmethyl p-Chlorocarbanilate (BTS-Fmoc-PCA): A mixture of 2.5 g of 2,7-bis-(trimethylsilyl)fluorene-9-methanol and 1.13 g of p-chlorophenyl isocyanate in 20 mL of dry benzene was heated in an oil bath at 80° C. for four hours. The mixture was cooled to room temperature, treated with 60 mL of Skelly B, and stirred for another 30 minutes. The precipitate was removed by filtration to give 3.60 g (99.3%) of the crude urethane as a white solid. Recrystallization from Skelly B gave 3.13 g (86.3%) of the 2,7-Bis(trimethylsilyl)-9-fluorenylmethyl p-chlorocarbanilate as white crystals, m.p. 162.5°–163.5° C.; IR (KBr : 3240 (NH), 1710 (C=O) cm$^{-1}$; $^1$H NMR (CDCl$_3$): δ 0.30 (s, 18H, SiMe$_3$), 4.28 (t, 1H, CH), 4.58 (d, 2H, CH$_2$), 6.60 (b, 1H, NH), 7.15–7.90 (m, 10H, aryl).

Anal. Calcd for C$_{27}$H$_{32}$NO$_2$Si$_2$Cl: C, 65.62; H, 6.53; N, 2.83. Found; C, 65.80; H, 6.66; N, 2.80.

EXAMPLE 41

2,7-Di-tert-butyl-9-Fluorenylmethyl p-Chlorocarbanilate (DT-Fmoc-PCA): A mixture of 0.916 g of 2,7-di-tert-butyl-9-fluorenemethanol and 0.456 g of p-chlorophenyl isocyanate in 4.0 mL of dry benzene was heated in an oil bath at 80° C. for 6 hours. The mixture was cooled to room temperature and the solvent was removed in vacuo to give an oil which was crystallized after trituration with 15 mL of Skelly B to afford 1.31 g (95.6%) of the crude urethane as a white solid. Recrystallization from Skelly B—acetone (4:1) gave 1.08 g (81.2%) of the pure DT-Fmoc-PCA as white crystals, m.p. 193°–194.5° C.; IR (KBr): 3400 (NH), 1735 (C=O) cm$^{-1}$; $^1$H NMR (CDCl$_3$) $\delta$ 1.37 (s, 18H, t-Bu), 4.22 (t, 1H, CH), 4.60 (d, 2H, CH$_2$), 6.63 (b, 1H, NH), 7.18–7.55 (m, 10H, aryl).

Anal. Calcd for C$_{29}$H$_{32}$NO$_2$Cl: C, 75.39; H, 6.98; N, 3.03. Found: C, 75.36; H, 6.87; N, 3.01.

EXAMPLE 42

2,7-Bis(trimethylsilyl)-9-methylfluorene: To a solution of 1.0 g of 2,7-bis(trimethylsilyl)fluorene in 15 mL of dry ether was added dropwise 2.8 mL of 1.3 M n-butyllithium at 0° C. The mixture was stirred at room temperature for 3 hours, cooled to 0° C., and treated with a solution of 0.25 mL of methyl iodide in 5 mL of dry ether over a period of 5 minutes. The mixture was stirred at room temperature for 8 hours and washed with 2% Na$_2$S$_2$O$_3$ (10 mL) and water (2×10 mL). The pooled aqueous layer was extracted with ether (2×15 mL). The combined organic extracts were dried over MgSO$_4$ and the solvent was evaporated under reduced pressure to give 1.03 g (98.7%) of the crude 2,7-bis(-trimethylsilyl)-9-methylfluorene as a yellow oil which was chromatographed on silica gel (230–400 mesh, 2×40-cm packed column) with an eluant consisting of Skelly B—dichloromethane (6:1) to give 0.78 g (74.7%) of the crude hydrocarbon as a colorless oil. Crystallization from 95% ethanol gave 0.69 g (66.1%) of the pure 2,7-bis(trimethyl-silyl)-9-methylfluorene as white needles, m.p. 107°–108.5° C.; $^1$H NMR (CDCl$_3$): $\delta$ 0.34 (s, 18H, SiMe$_3$), 1.58 (d, 3H, CH$_3$), 3.96 (q, 1H, CH), 7.40–7.90 (m, 6H, aryl).

Anal. Calcd for C$_{20}$H$_{28}$SiO$_2$: C, 74.00; H, 8.69; Found: C, 73.91; H, 8.51.

C. Mixed Substitutions

EXAMPLE 43

2,7-Bis(trimethylsilyl]-9-fluorenylmethyl Chloroformate: To a stirred solution of 1 mL of liquid phosgene, condensed at −78° C., in 10 mL of dry THF was added dropwise a solution of 2.0 g of 2,7-bis(trimethylsilyl)-9-fluorenemethanol in 20 mL of dry THF at 0° C. for 30 minutes. The mixture was stirred for another hour at 0° C. The excess phosgene along with the solvent was removed by a water aspirator in a hood to afford an oil which was triturated with Skelly F to give 2.3 g (97.1%) of the crude chloroformate as white crystals. Recrystallization from Skelly F gave 2.02 g (85.23%) of the pure chloroformate as colorless crystals, m.p. 64°–66° C.; IR (KBr): 1770 cm$^{-1}$ (C=O); $^1$H NMR (CDCl$_3$): $\delta$ 0.37 (s, 18H, SiMe$_3$), 4.32 (t, 1H, CH), 4.57 (d, 2H, CHO$_2$), 7.50–7.90 (m, 6H, aryl).

Anal. Calcd for C$_{21}$H$_{27}$O$_2$Si$_2$Cl: C, 62.58; H, 6.75. Found: C, 62.79; H, 6.74.

EXAMPLE 44

1. 2,7-Di(t-butyl)-9-trimethylsilylfluorene: To a solution of 10 g of 2,7-di-tert-butylfluorene in 120 mL of dry ether was added dropwise 30 mL of 1.4M n-butyllithium over a period of 20 minutes. The mixture was refluxed for five hours, cooled to room temperature, and treated with 5.5 mL of chlorotrimethylsilane in one portion. The mixture was refluxed for 3 hours, cooled to 0° C., and quenched with 20 mL of sat'd NH$_4$Cl. The organic layer was washed with water (2×30 mL) and the pooled aqueous layer was extracted with ether (2×40 mL). The combined organic extracts were dried over MgSO$_4$ and the solvent was evaporated in vacuo to give 12.60 (100%) of the crude silane as a yellow solid. Recrystallization from EtOH—EtOAc (4:1) afforded 10.43 g (82.7%) of the pure 2,7-di(t-butyl)-9-trimethylsilylfluorene $^1$H NMR (CDCl$_3$): $\delta$ −0.07 as white crystals, m.p. 144°–145.5° C.; $^1$H NMR (CDCl$_3$): $\delta$ −0.07 (s, 9H, SiMe$_3$), 1.39 (s, 18H, t-Bu), 3.80 (s, 1H, CH), 7.20–7.80 (m, 6H, aryl).

Anal. Calcd for C$_{24}$H$_{34}$Si: C, 82.22; H, 9.77. Found: C, 82.51; H, 10.09.

2. 2,7-Di(t-butyl)-9-trimethylsilyl-9-fluorenylmethyl Benzyl Ether: To a solution of 2,7-di(t-butyl)-9-trimethylsilylfluorene in 100 mL of dry ether was added dropwise 9.2 mL of 2.4M n-butyllithium. The mixture was refluxed for 3 hours, cooled in an ice bath, and treated with 3.1 mL of freshly distilled benzyl chloromethyl ether in one portion. The mixture was stirred at room temperature for 1 hour and quenched with 20 mL of sat'd NH$_4$Cl. The organic layer was washed with water (50 mL) and the pooled aqueous layer was extracted with ether (2×40 mL). The combined organic extracts were dried over MgSO$_4$ and the solvent was evaporated under reduced pressure to give 9.39 g (100%) of the crude benzyl ether as an off-white solid. Recrystallization from EtOH—EtOAc (10:1) gave 6.37 g (67.8%) of the pure 2,7-di(t-butyl)-9-trimethylsilyl-9-fluorenylmethyl benzyl ether as white crystals, m.p. 100°–101.5° C.; $^1$H NMR (CDCl$_3$): $\delta$ −0.18 (s, 9H, SiMe$_3$), 1.40 (s, 18H, t-Bu), 4.07 (s, 2H, C—CH$_2$O), 4.57 (s, 2H, OCH$_2$Ar), 7.20–7.80 (m, 11H, aryl).

Anal. Calcd. for C$_{32}$H$_{42}$SiO: C, 81.64; H, 8.99. Found: C, 81.79; H, 8.95.

EXAMPLE 45

2,7-Di-tert-butyl-9-trimethylsilyl-9-fluorenemethanol: To a solution of 4.0 g of 2,7-di-tert-butyl-9-trimethylsilyl-9-fluorenylmethyl benzyl ether in 20 mL of freshly distilled THF and 80 mL of 100% EtOH was added 0.8 g of 5% palladium on charcoal. The heterogeneous mixture was shaken under hydrogen at a pressure of 45 psi in a Parr apparatus for 2 hours. The catalyst was removed by filtration and rinsed with ether (2×10 mL). The filtrate was evaporated under reduced pressure to give 3.23 g (100%) of the crude alcohol as a yellow oil which was chromatographed on silica gel (230–400 mesh, 4×45-cm packed column) with an eluant consisting of Skelly B—ether (3:1), to give 3.12 g (96.4%) of the alcohol as a white solid. Recrystallization from Skelly B gave 2.57 g (79.44%) of the pure alcohol as white needles, m.p. 131°–132° C.; IR (KBr): 3545, 3495 cm$^{-1}$ (OH); $^1$H NMR (CDCl$_3$): $\delta$ −0.18 (s, 9H, SiMe$_3$), 1.20 (b, 1H, OH), 1.39 (s, 18H, t-Bu), 4.50 (s, 2H, CH$_2$), 7.20–7.90 (m, 6H, aryl).

Anal. Calcd for $C_{25}H_{36}SiO$: C, 78.89; H, 9.53. Found: C, 79.08; H, 9.71.

D. Difluorenes

EXAMPLE 46

2,7-Di-tert-butyl-9-trimethylsilyl-9-fluorenylmethyl Carbanilate (DT-TMS-Fmoc-aniline): A mixture of 1.0 g of 2,7-di-tert-butyl-9-trimethylsilyl-9-fluorenemethanol and 0.28 mL of phenyl isocyanate in 10 mL of dry benzene was heated in an oil bath at 84° C. for 24 hours. The mixture was cooled to room temperature and the solvent was evaporated under reduced pressure to give an oil which was chromatographed on silica gel (230–400 mesh, 2.5×40-cm packed column) with an eluant consisting of Skelly B—ether (3:1) to afford 1.22 g (94.8%) of the crude urethane as a white solid. Recrystallization from Skelly B gave 1.03 g (80.0%) of the pure DT-TMS-Fmoc-aniline as colorless crystals, m.p. 94°-96° C.; IR (KBr): 3330 (NH), 1705 (C=O) cm$^{-1}$; $^1$H NMR (CDCl$_3$): δ −0.16 (s, 9H, SiMe$_3$), 1.38 (S, 18H, t-Bu), 5.09 (s, 2H, CH$_2$), 6.25 (b, 1H, NH), 6.80–7.80 (m, 11H, aryl).

Anal. Calcd for $C_{32}H_{41}NO_2Si$: C, 76.91; H, 8.27; N, 2 80. Found: C, 76.82; H, 8.23; N, 2.63.

EXAMPLE 47

A. Benzyl 9-fluorenylmethyl Ether: To a solution of 20 g of fluorene in 400 mL of ether was added dropwise 85 mL of 1.5M n-butyllithium over a period of 45 minutes. The mixture was refluxed for 3 hours, cooled to 0° C., and treated dropwise with 17.5 mL of freshly distilled benzyl chloromethyl ether over a period of 20 minutes. The mixture was stirred at 0° C. for one hour, quenched with half sat'd NH$_4$Cl (100 mL), and washed with water (100 mL). The pooled aqueous layer was extracted with ether (2×100 mL). The combined organic extracts were dried over MgSO$_4$ and the solvent was evaporated under reduced pressure to afford a yellow oil which was distilled in vacuo, b.p. 165°–168° C. (0.015 mmHg), to afford 31.46 g (91.24%) of the crude benzyl ether which soon solidified. Recrystallization from 95% EtOH—EtOAc (10:1) gave 23.45 g (68.0%) of the pure benzyl 9-fluorenylmethyl ether as white crystals, m.p. 69.5°–70° C.; $^1$H NMR (CDCl$_3$): δ 3.75 (d, 2H, CH-CH$_2$O), 4.22 (t, 1H, CH), 4.62 (s, 2H, OCH$_2$Ar).

Anal. Calcd for $C_{21}H_{18}O$: C, 88.08; H, 6.34. Found C, 87.68; H, 6.32.

B. Bis(9-fluorenyl)methane: To a solution of 10 g (60.24 mmol) of fluorene in 80 mL of freshly distilled THF was added dropwise 26 mL of 2.4M n-butyllithium. The mixture was refluxed for 3 hours, cooled to room temperature, and treated dropwise with two solutions: (a) 11.5 g (40.2 mmol) of benzyl 9-fluorenylmethyl ether in 80 mL of dry THF, and (b) 17.5 mL of 2.4M n-butyllithium. The two solutions were added together over a period of 1 hour. The resulting mixture was refluxed for 42 hours, cooled in an ice bath, and quenched with 100 mL of half sat'd NH$_4$Cl. The organic phase was washed with water (50 mL) and the precipitated solid was removed by filtration to give 7.04 g of an off-white solid. The filtrate was dried over MgSO$_4$ and the solvent was evaporated in vacuo to give an oil which was triturated with ether to give an additional 6.31 g of yellowish solid. Recrystallization of the combined crude hydrocarbon (13.35 g, 96.6%) from CHCl$_3$—Skelly B (3:1) gave 11.46 g (82.9%) of the pure bis (9-fluorenyl)methane as white crystals, m.p. 210°–212° C.; $^1$H NMR (CDCl$_3$): δ 2.22 (t, 2H, CH$_2$), 4.37 (t, 2H, CH), 7.05–7.92 (m, 16H, aryl).

EXAMPLE 48

9-(9'-Fluorenylmethyl)-9-fluorenylmethyl Benzyl Ether: To a suspension of 1.5 g of bis-(9-fluorenyl)methane in 20 mL of freshly distilled THF and 40 mL of dry ether was added 3.3 mL of 1.45M n-butyllithium in one portion at 0° C. The mixture was refluxed for 5 hours, cooled in an ice bath, and treated in one portion with 0.6 mL of freshly distilled benzyl chloromethyl ether. The mixture was warmed to room temperature gently, stirred for another 90 minutes, and quenched with 60 mL of half sat'd NH$_4$Cl. The organic layer was washed with water (60 mL) and the pooled aqueous layer was extracted with ether (2×50 mL). The combined organic extracts were dried over anhydrous MgSO$_4$ and the solvent was evaporated under reduced pressure to give 1.98 g (98.75%) of the crude benzyl ether as an off-white solid. Recrystallization twice from EtOAc gave 1.24 g (61.9%) of the pure 9-(9'-fluorenylmethyl)-9-fluorenylmethyl benzyl ether as white crystals, m.p. 177°–178.5° C.; $^1$H NMR (CDCl$_3$): δ 2.92 (d, 2H, CH—CH$_{2O}$), 3.25 (t, 1H, CH), 3.67 (s, 2H, C—CH$_2$O), 4.51 (s, 2H, OCH$_2$Ar), 6.55–8.00 (m, 21H, aryl).

Anal. Calcd for $C_{35}H_{28}O$: C, 90.48, H, 6.07. Found: C, 90.22; H, 6.11.

EXAMPLE 49 15

9-(9'-Fluorenylmethyl]-9-fluorenemethanol): To a solution of 1.0 g of 9-(9'-fluorenylmethyl)-9-fluorenylmethyl benzyl ether in 80 mL of freshly distilled THF and 20 mL of 100% ethanol was added 0.2 g of 5% palladium on charcoal. The heterogeneous mixture was shaken under hydrogen at a pressure of 45 psi in a Parr apparatus for 24 hours. The catalyst was removed by filtration and rinsed with ether (2×5 mL). The filtrate was evaporated in vacuo to give 0.75 g (93.3%) of the crude alcohol as a white solid. Recrystallization from Skelly B—EtOAc (3:1) gave 0.51 g (63.4%) of the pure 9-(9'-fluorenylmethyl)-9-fluorenemethanol as white crystals, m.p. 180°–182° C.; IR (KBr): 3560 cm$^{-1}$ (OH); $^1$H NMR (CDCl$_3$): δ 1.55 (s, 1H, OH), 2.75 (d, 2H, CH—CH$_2$O), 3.25 (t, 1H, CH), 3.79 (s, 2H, CCH$_2$O), 6.35–7.95 (m, 16H, aryl).

Anal. Calcd for $C_{28}H_{22}O$: C, 89.81; H, 5.92. Found C, 89.63; H, 5.88.

EXAMPLE 50

9-(9'-Fluorenylmethyl)-9-fluorenylmethyl Carbanilate (FM-Fmoc-aniline): A solution of 0.21 mL of phenyl isocyanate and 0.75 g of 9-(9'-fluorenylmethyl)-9-fluorenemethanol in 4 mL of dry THF and 8.0 mL of dry benzene was heated in an oil bath at 82° C. for 4 hours, and cooled to room temperature. The solvent was evaporated in vacuo and the residue was triturated with Skelly B to give 0.93 g (97.52%) of the crude urethane as a white solid. Recrystallization from EtOAc gave 0.67 g (70.26%) of the pure FM-Fmoc-aniline as white needles, m.p. 243°–244° C.; IR (KBr): 3422 (NH), 1732 (C=O) cm$^{-1}$; $^1$H NMR (DMSO-d$_6$): δ 2.81 (d, 2H, CH—CH$_2$C), 2.95 (t, 1H, CH), 4.41 (s, 2H, CCH$_{2O}$), 6.50–8.10 (m, 21H, aryl), 9.57 (b, 1H, NH).

Anal. Calcd for $C_{35}H_{27}NO_2$: C, 85.17; H, 5.51: N, 2.81. Found: C, 84.95; H, 5.49; N, 2.78.

EXAMPLE 51

9-(9'-Fluorenylmethyl)-9-fluorenylmethyl p-Chlorocarbanilate (FM-Fmoc-PCA): To a mixture of 1.0 g of 9-(9'-fluorenylmethyl)-9-fluorenemethanol and 0.42 g of p-chlorophenyl isocyanate in 6 mL of freshly distilled THF and 12 mL of dry benzene was added 2 drops of triethylamine. The mixture was heated in an oil bath at 80° C. for 12 hours, cooled to room temperature, and the solvent was evaporated under reduced pressure to give 1.40 g (100%) of the crude urethane as a white solid. Recrystallization from EtOAc— Skelly B (2:1) gave 1.02 g (72.7%) of the pure FM-Fmoc-PCA as white crystals, m.p. 215°-217° C.; IR (KBr): 3260 (NH), 1700 =O) cm$^{-1}$, $^1$H NMR (CDCl$_3$): δ 2.80 (d, 2H, CH—CH$_2$), 3.19 (t, 1H, CH), 4.51 (s, 2H, CH$_2$O), 6.57 (b, 1H, NH), 6.55-7.95 (m, 20H, aryl).

Anal. Calcd for C$_{35}$H$_{26}$NO$_2$Cl: C, 79.61; H, 4.61; N, 2.65. Found: C, 79.31; H, 4.94; N, 2.79.

EXAMPLE 52

Bis(9-fluorenyl)methyl Chloroformate: To an ice-cold solution of 1.5 g of bis(9-fluorenyl)methanol in 30 mL of dry THF was added 1.5 mL of liquid phosgene, condensed at −78° C. The mixture was stirred under a nitrogen atmosphere for seven days. The excess phosgene along with the solvent was removed by a water aspirator in a hood to give 1.75 g (99.4%) of the crude chloroformate as a white solid. Recrystallization from CHCl$_3$—Skelly B (2:1) gave 1.18 g (67.02%) of the pure bis(9-fluorenyl)methyl chloroformate as white crystals, m.p. 179° C. (dec.); IR (KBr): 1770 (C=O) cm$^{-1}$; $^1$H NMR (CDCl$_3$): δ 4.62 (d, 2H, ArCH), 5.69 (t, 1H, CHO), 7.15-7.95 (m, 16H, aryl).

Anal. Calcd for C$_{28}$H$_{19}$O$_2$Cl: C, 79.52; H, 4.53; Cl, 8.38. Found: C, 79.31; H, 4.55; Cl, 8.07.

EXAMPLE 53

Bis(9-fluorenyl)methyl Carbanilate (α-F-Fmoc-aniline): To a solution of 1.0 g (1.18 mmol) of bis(9-fluorenyl)-methyl chloroformate in 15 mL of freshly distilled THF and 15 mL of dry benzene was added 0.21 mL (2.3 mmol) of freshly distilled aniline in one portion at 0° C. The mixture was stirred at 0° C. for 3 hours and quenched with 10 mL of sat'd NH$_4$Cl. The organic layer was washed with water (10mL) and the pooled aqueous layer was extracted with CHCl$_3$ (2×10 mL). The combined organic extracts were dried over MgSO$_4$ and the solvent was evaporated in vacuo to give 1.13 g (100%) of the crude urethane as a white solid. Recrystallization from chloroform gave 0.93 g (82.03%) of the pure α-F-Fmoc-aniline as white crystals, m.p. 225°-227° C. (dec.); IR (KBr): 3340 (NH), 1705 (C=O) cm$^{-1}$; $^1$H NMR (DMSO-d$_6$): δ 4.59 (d, 2H, ArCH), 5.70 (t, 1H, CHO), 6.80-7.95 (m, 21H, aryl), 9.38 (b, 1H, NH).

Anal. Calcd for C$_{34}$H$_{25}$NO$_2$: C, 85.15; H, 5.25; N, 2.92. Found: C, 84.91; H, 5.14; N, 2.89.

Preparation of Blocked Amino Acids

EXAMPLE 54

9-Xanthenylmethoxycarbonyl-L-phenylalanine (Xmoc-Phe-OH): To a suspension of 0.467 g of L-phenylalanine and 0.6 g of sodium carbonate in 6 mL of water and 6 mL of dioxane was added dropwise at 0° C. a solution of 1.0 g of succinimidyl 9-xanthenylmethyl carbonate in 10 mL of dioxane over a period of 10 minutes. The mixture was stirred at room temperature for four hours, washed with ether (2×15 mL), and the ether layer was discarded. The aqueous layer was acidified with 10% HCl (Congo Red) and extracted with EtOAc (3×15 ml). The combined organic extracts were dried over MgSO$_4$ and the solvent was evaporated in vacuo to give 1.02 g (89.43%) of the crude Xmoc-Phe-OH as a colorless oil. Crystallization from Skelly B -EtOAc (3:1) gave 0.77 g (67.51%) of the pure Xmoc-Phe-OH as white crystals, m.p. 143°-145° C.; IR KBr: 3420 (NH and OH), 1720 (C=O)cm$^{-1}$; $^1$H NMR (CDCl$_3$): δ 2.90-3.30 (m, 2H, CH$_2$Ar), 4.40-4.45 (m, 3H, CH—CH$_2$O), 4.65 (m, 1H, NCH), 5.18 (b, 1H, NH), 6.85-7.60 (m, 13H, aryl); [α]$^{23}$ D −3.1 (c=1, EtOAc), [α]$^{23}$546 −3.4 (c=1, EtOAc).

Anal. Calcd for C$_{24}$H$_{21}$NO$_5$: C, 71.45; H, 5.25; N, 3.47. Found: C, 71.37; H, 5.05; N, 3.41.

EXAMPLE 55

N$^\epsilon$-(9-Xanthenylmethoxycarbonyl)-L-lysine (H-Lys(Xmoc)-OH): A mixture of 4.0 g of L-lysine hydrochloride and 2.6 g of basic copper carbonate suspended in 60 mL of water was refluxed for 20 minutes and cooled to room temperature. The precipitate was filtered, rinsed with water (2×15 mL) and discarded. The combined filtrate was cooled in an ice bath, diluted with 250 mL of DMF and treated in one portion with 3.5 g of sodium bicarbonate and 7.2 g of succinimidyl 9-xanthenylmethyl carbonate. The mixture was stirred at room temperature for 16 hours. The resulting blue precipitate was filtered and rinsed with water (5 mL) and ethanol (5 mL). The blue copper complex was suspended in 300 mL of water and 10 mL of ethanol, treated with 20 g of ethylenediaminetetraacetic acid disodium salt, and the mixture refluxed for 20 minutes. After cooling at 0° C. for 30 minutes, the white precipitate was filtered, rinsed with H$_2$O (15 mL) and ethanol (10 mL), and dried in air to give 8.02 g (97.8%) of H-Lys(Xmoc)-OH as white crystals, m.p. 220°-221° C. (dec.); IR (KBr): 3350 (b, NH and OH), 1700 (C=O) cm$^{-1}$; $^1$H NMR (DMSO-d$_6$): δ 1.05-1.78 (m, 6H, CH$_2$CH$_2$CH$_2$), 2.70-2.97 (b, 2H, CH$_2$N), 3.18 (b, 1H, CHN), 4.04 (d, 2H, CH$_2$O), 4.31 (t, 1H, ArCHAr), 6.70-8.00 (m, 12H, aryl and amino); [α]$^{25}$D 7.8 (c=1, 1N HCl), [α]$^{25}$546 9.1 (c=1, 1N HCl).

Anal. Calcd for C$_{21}$H$_{24}$N$_2$O$_5$.H$_2$O: C, 62.67; H, 6.51; N, 6.96. Found: C, 62.99; H, 6.32; N, 6.93.

Synthesis of a Pentapeptide From Thymopoietin

EXAMPLE 56

The pentapeptide corresponding to positions 32-36 (arginyllysylaspartylvalytyrosine; TPS) of thymopoietin was synthesized to examine the utility of Xmoc as a side chain protecting group. The peptide was assembled using continuous flow, Fmoc-based N$^\alpha$ chemistry using a Milligen 9050 automated synthesizer. This approach employed pentafluorophenyl esters as convenient acylating agents. The individual amino acid derivatives used in the synthesis of TP5 are shown in Table 1A. The synthetic routes to the derivatives of Lys, Val, and Asp are described below. The other derivatives are commercially available from the Milligen Division of Millipore, Inc.

The final pentapeptide was isolated by treatment with trifluoroacetic acid (TFA) first to detach from the resin and deblock all the acid-sensitive protecting groups in one step. The remaining Xmoc function on lysine of the pentapeptide was then deblocked by TBD in a mixture of DMF and pyridine.

A. Fmoc-Lys(Xmoc)-Opfp:

1. 9-Fluorenylmethyl Chloroformate: To an ice-cold solution of 45 mL of liquid phosgene, condensed at −78° C., in 50 mL of freshly distilled THF was added dropwise a solution of 30 g of 9-fluorenemethanol in 150 mL of freshly distilled THF over a period of 30 minutes. The mixture was stirred at room temperature for 90 minutes. Excess phosgene along with the solvent was evaporated in a hood with the aid of a water aspirator to give 38.6 g (100%) of the crude chloroformate. Recrystallization from Skelly F—ether (9:1) gave 37.9 g (95.8%) of the pure 9-fluorenylmethyl chloroformate as white needles, m.p. 62°–63° C.; IR (KBr): 1760 (C=O) cm$^{-1}$; $^1$H NMR (CDCl$_3$): $\delta$ 4.33 (t, 1H, CH), 4.57 (d, 2H, CH$_2$), 7.22–7.87 (m, 8H, aryl).

2. Succinimidyl 9-Fluorenylmethyl Carbonate (Fmoc-OSu): To a mixture of 20 g of 9-fluorenylmethyl chloroformate and 9 g of N-hydroxysuccinimide in 200 mL of freshly distilled THF was added dropwise at −78° C. a solution of 10.5 mL of triethylamine in 80 mL of dry THF over a period of 40 minutes. The mixture was stirred at −78° C. for 2 hours. The precipitated salt, Et$_3$N.HCl, was filtered and rinsed with THF (2×30 ml). The filtrate was evaporated in vacuo to give 25.4 g (100%) of the crude carbonate as a white solid. Recrystallization from ether—CHCl$_3$ (4 1) gave 24.5 g pure Fmoc-OSu as white needles, m.p. (96.5%) of the pure Fmoc-OSu as white needles, m.p. 149°–151° C.; IR (KBr): 1810, 1780, 1740 (C=O) cm$^{-1}$; $^1$H NMR (CDCl$_3$): $\delta$ 2.82 (s, 4H, CH$_2$CH$_2$), 4.38 (t, 1H, CH), 4.59 (d, 2H, CH$_{2O}$), 7.15–7.90 (m, 8H, aryl).

3. 9-Fluorenylmethoxycarbonyl-N$^\epsilon$-(9-xanthenylmethoxycarbonyl)- L-lysine (Fmoc-Lys(Xmoc)-OH): To a suspension of 1.0 g of Ns-Xmoc-Lysine monohydrate and 0.8 g of sodium carbonate in 16 mL of water and 6 mL of dioxane was added dropwise a solution of 1.0 g of succinimidyl 9-fluorenylmethyl carbonate in 10 mL of dioxane. The mixture was stirred at room temperature for 16 hours, washed with ether (2×60 mL) and the ether layer discarded. The aqueous layer was acidified with 4N HCl (Congo Red), and extracted with EtOAc (3×20 mL). The combined extracts were dried over MgSO$_4$ and the solvent evaporated under reduced pressure to afford 1.5 g (100%) of an oil which was triturated with Skelly B to afford 1.45 g (96.2%) of the crude Fmoc-amino acid as a white solid. Recrystallization from ether—EtOAc (2:1) gave 1.24 g (82.3%) of the pure Fmoc-Lys-(Xmoc)-OH as white crystals, m.p. 128°–130° C.; IR (KBr): 3355 (NH and OH), 1750, 1695 (C=O) cm$^{-1}$; $^1$H NMR (CDCl$_3$): $\delta$ 1.15–1.95 (m, 6H, CH$_2$—CH$_2$CH$_2$), 2.82–3.17 (m, 2H, CH$_2$N), 4.15–4.60 (m, 6H, CHCH$_2$O), 4.80 (s, 1H, CHN), 5.70, 6.41 (b, 2H, NH), 6.95–7.90 (m, 16H, aryl); [$\alpha$]$^{23}$D −20.2 (c=1, MeOH), [$\alpha$]$^{23}$$_{23}$546 24.2 (c=1, MeOH).

Anal. Calcd for C$_{36}$H$_{34}$N$_2$O$_7$: C, 71.27; H, 5.65; N, 4.62. Found: C, 71.15; H, 5.49; N, 4.52.

4. Pentafluorophenyl 9-Fluorenylmethoxycarbonyl-N$^\epsilon$-(9-xanthenylmethoxycarbonyl)-L-lysinate (Fmoc-Lys(Xmoc)-Opfp): To a mixture of 1.3 g of Fmoc-Lys(Xmoc)-OH and 0.43 g of pentafluorophenol in 15 mL of freshly distilled THF was added 0.49 g of dicyclohexylcarbodiimide. The mixture was stirred at room temperature for 4.5 hours and the precipitated dicyclohexylurea (DCU) was removed by filtration and discarded. The solvent was evaporated in vacuo to afford a white oil which was triturated with Skelly B—ether (3:1) to give 1.60 g (96.6%) of the crude active ester as a white solid. Recrystallization from Skelly B—EtOAc (2:1) gave 1.40 g (84.54%) of the pure Fmoc-Lys(Xmoc)-Opfp as white crystals, m.p. 150°–152° C.; IR (KBr): 3315 (NH and OH), 1783, 1720, 1690 (C=O)cm$^{-1}$; $^1$H NMR (CDCl$_3$): $\delta$1.20–2.15 (m, 6H CH$_2$—CH$_2$CH$_2$), 3.10–3.25 (m, 2H, CH$_2$N), 4.10–4.85 (m, 6H, CHCH$_2$O), 5.55 (d, 1H, NH), 6.95–7.90 (m, 17H, aryl and NH); [$\alpha$]$^{24}$D −13.8 (c=1, CH$_2$Cl$_2$), [$\alpha$]$^{24}$546 −16.9 (c=1, CH$_2$Cl$_2$).

Anal. Calcd for C$_{42}$H$_{33}$N$_2$O$_7$F$_5$: C, 65.28; H, 4.30; N, 3.63. Found: C, 65.18; H, 4.31; N, 3.62.

B. Fmoc-Val-Opfp:

1. 9-Fluorenylmethoxycarbonylvaline (Fmoc-Val-OH): To a mixture of 1.0 g of L-valine and 2.0 g of Na$_2$CO$_3$ in 40 mL of water and 10 mL of dioxane was added dropwise a solution of 3.2 g of succinimidyl 9-fluorenylmethyl carbonate in 30 mL of dioxane over a period of 20 minutes. The mixture was stirred at room temperature for 16 hours, washed with ether (2×50 mL), and the ether layer was discarded. The aqueous layer was neutralized with 6N HCl (Congo Red) and extracted with EtOAc (3×50 mL). The combined organic extracts were dried over anhydrous MgSO$_4$, and the solvent was evaporated in vacuo to give 2.90 g (100%) of the Fmoc amino acid as a white solid. Recrystallization from Skelly B—EtOAc (2:1) gave 2.62 g (90.44%) of the Fmoc-Val-OH as white crystals, m.p. 141°–143° C.; IR (KBr) 3385 (NH and OH), 1725 (C=O) cm$^{-1}$; $^1$H NMR (CDCl$_3$): $\delta$ 0.94 (d, 3H, CH$_3$), 1.02 (d, 3H, CH$_3$), 2.22 (m, 1H, CH-Me$_2$), 4.22 (t, 1H, CH-Ar$_2$), 4.40 (m, 1H, CH-N), 4.41 (d, 2H, CH$_2$O), 5.28 (d, 1H, NH), 7.20–7.85 (m, 8H, aryl); [$\alpha$]$^{24}$D −6.8 (c=1, MeOH), [$\alpha$]$^{24}$546 7.8 (c=1, MeOH).

2. Pentafluorophenyl 9-Fluorenylmethoxycarbonylvalinate (Fmoc-Val-Opfp): To a solution of 1.5 g of 9-fluorenylmethoxycarbonylvaline in 20 mL of freshly distilled THF was added 1.7 g of pentafluorophenol and 1.0 g of dicyclohexylcarbodiimide. The mixture was stirred at room temperature for five hours and the precipitated dicyclohexylurea was removed by filtration. The filtrate was evaporated in vacuo to give an oil which was triturated with Skelly B to give 2.24 g (100%) of the crude ester as an off-white solid. Recrystallization from EtOAc—Skelly B gave 1.95 g (87.3%) of the pure Fmoc-Val-Opfp as colorless crystals, m.p. 122°–124° C.; IR (KBr): 3380 (NH and OH), 1790, 1710 (C=O) cm$^{-1}$; $^1$H NMR (CDCl$_3$): $\delta$ 1.02 (d, 3H, CH$_3$), 1.11 (d, 3H, CH$_3$), 2.39 (m, 1H, CH-Me$_2$), 4.22 (t, 1H, CH—Ar$_2$), 4.49 (d, 2H, CH$_2$O), 4.69 (m, 1H, CH-N), 5.27 (d, 1H, NH), 7.20–7.85 (m, 8H, aryl); [$\alpha$]$^{24}$D −26.2 (c=1, CH$_2$Cl$_2$), [$\alpha$]$^{24}$546 −31.0 (c=1, CH$_2$Cl$_2$).

C. Fmoc-Asp(O$^t$Bu)-Opfp $\alpha$-Pentafluorophenyl, $\beta$-tert-Butyl 9-Fluorenylmethoxycarbonyl-L-aspartate (Fmoc-Asp(O$^t$Bu)-Opfp): To a solution of 1.0 g of $\beta$-tert-butyl 9-fluorenylmethoxycarbonyl-L-aspartate in 15 mL of freshly distilled THF was added 0.56 g of pentafluorophenol and 0.56 g of DCC. The mixture was stirred at room temperature for 5 hours. The precipitated DCU was removed by filtration and the solvent was evaporated in vacuo to give 1.42 g (100%) of yellowish oil which was triturated with Skelly F to afford 0.93 g (66.3%) of the crude active ester as a white solid. Recrystallization from Skelly F gave 0.74 g (52.7%) of the Fmoc-Asp(O$^t$Bu)-Opfp): To a colorless solid, m.p. 94°–96° C.; IR (KBr):

3330 (NH), 1790, 1725 (C=O)cm$^{-1}$; $^1$H NMR (CDCl$_3$): δ 1.50 (s, 9H, t-Bu), 3.04 (dd, 2H, CH ), 4.28 (t, 1H, ArCHAr), 4.34–4.56 (m, 2H, CH$_2$O), 5.00 (m, 1H, N-CH), 5.98 (d, 1H, NH), 7.22–7.83 (m,

24546 -2.9 (c=1, 8H, aryl); [α]$^{24}$D −2.2 (c=1, chloroform), [α]$^{24}$546 −2.9 (c=1, chloroform).

Anal. Calcd for C$_{29}$H$_{24}$NO$_6$F$_5$; : C, 60.31; H, 4.19; N, 2.43. Found: C, 60.22; H, 4.14; N, 2.33.

D. Assembly of TP5 (Arginyllysylaspartylvalyltyrosine)

To the reaction vessel of a Milligen 9050 automated synthesizer was added 1.0 g (0.090 meq/g) of Fmoc-Tyr(O-t-Bu)-KA resin and DMF was allowed to flow through the system at a rate of 3.0 mL/min for 5 minutes with occasional shaking to remove all air bubbles. To the racks of the amino acid module were attached four vials filled separately with the amino acid derivatives shown in Table 1B. The synthesis protocol was programmed via a NEC PowerMate-1-Plus personal computer as shown in Table 1C. This synthesis cycle was repeated four times to give Fmoc-Arg(Mtr)-Lys(Xmoc)-Asp(O-t-Bu)-Val-Tyr-(O-t-Bu)-KA resin which was treated with piperidine at a rate of 3.0 mL/min for 7 minutes and washed with DMF (3.0 mL/min) for 12 minutes and dichloromethane (3.0 mL/min) for 15 minutes to give H-Arg(Mtr)-Lys(Xmoc)-Asp(O-t-Bu)-Val-Tyr(O-t-Bu)-KA resin. The reaction vessel was disconnected from the synthesizer and the resin was filtered (sintered glass funnel), washed with n-amyl alcohol (2×10 mL), acetic acid (2×10 mL), n-amyl alcohol (10 mL) and ether (4×10 mL), dried in air and treated with a mixture of 10 mL of TFA and 0.5 g of phenol at room temperature for 3 hours. The resin was removed by filtration and the filtrate was evaporated in vacuo with a water bath temperature not to exceed 45° C. to give an orange oil which was triturated with ether (8 mL) to afford 68 mg (82.30%) of H-Arg-Lys(Xmoc)-Asp-Val-Tyr-OH as a white solid. The crude Xmoc-protected peptide was treated with 1.0 g of TBD (97.0 eq.) in a solution of 4 mL of DMF and 4 mL of pyridine. After standing at room temperature for 1 hour the solution was poured into 80 mL of ethyl acetate and stirred from another hour. The white precipitate was filtered and washed with ether (4×10 mL) to give 49 mg (80.33%) of the crude TP5 as an off-white solid which was purified by column chromatography on silica gel (230–400 mesh, 1.5×30-cm packed column) with a eluant consisting of n-BuOH: EtOAc: HOAc: H$_2$O=1:1:1:1 to give 42 mg (68.85%) of the arginyllysylaspartylvalyltyrosine as a white solid. HPLC analysis was carried out on a Waters Radial Pak 10-μm C$_{18}$ reverse phase column (0.8×10 cm) under the following conditions:

Mobile phase: 75% CH$_3$CN and 25% TFA (0.1% in water)
Flow rate: 1 mL/min
Injection volume: 15 μL
Detector: 254 nm The pentapeptide showed a retention time of 4.86 min (82.28%) along with a minor impurity at 5.73 min. The main peak agreed with that of authentic TP5 prepared in the same way using Fmoc-Lys(BOC)-Opfp by the standard technique.

TABLE 1A

| Amino Acid Derivatives Used in the Synthesis of TP5 | |
|---|---|
| Amino acid | Derivative used in SPPS |
| Tyrosine | Fmoc—Tyr (O$^t$Bu)—KA resin |

TABLE 1A-continued

| Amino Acid Derivatives Used in the Synthesis of TP5 | |
|---|---|
| Amino acid | Derivative used in SPPS |
| Valine | Fmoc—Val—Opfp |
| Aspartic acid | Fmoc—Asp(O$^t$Bu)—Opfp |
| Lysine | Fmoc—Lys(Xmoc)—Opfp |
| Arginine | Fmoc—Arg(Mtr)—Opfp |

TABLE 1B

| Amount of Amino Acid Derivatives Used in the Synthesis of TP5 | | | |
|---|---|---|---|
| Rack # | Amino acid derivative | Weight (g) | Equivalents |
| 1 | Fmoc—Val—Opfp | 0.128 | 4 |
| 2 | Fmoc—Asp(O-t-Bu)—Opfp | 0.208 | 4 |
| 3 | Fmoc—Lys(Xmoc)—Opfp | 0.278 | 4 |
| 4 | Fmoc—Arg(Mtr)—Opfp | 0.291 | 4 |

TABLE 1C

| Synthesis Protocol Used in the Preparation of TP5 | | | |
|---|---|---|---|
| Step | Operation | Rate | Duration |
| 01 | Piperidine wash | 3.0 mL/min | 7 min |
| 02 | DMF wash | 3.0 mL/min | 12 min |
| 03 | Recycle | 3.0 mL/min | 30 min |
| 04 | DMF wash loop | 3.0 mL/min | 8 min |
| 05 | DMF + HOBT wash probe | 10.0 mL/min | 1 min |

Deblocking and Stability Studies

EXAMPLE 57

Xanthene and Dihydroanthracene derivatives A. 9-Xanthenylmethyl derivatives

1. Deblocking of Xmoc-PCA in 1,5,9-Triazabicyclo[4,4,0]dec-5-ene Solution: To a solution of 7.90 mg (0.0216 mmol) of Xmoc-PCA in 0.6 mL of pyridine was added 0.15 g (1.078 mmol 50 eq.) of 1,5,9-triazabicyclo[4,4,0]dec-5-ene (TBD). The mixture was stirred at room temperature and monitored by TLC with an eluant consisting of Skelly B—EtOAc (3:1). Complete deblocking had occurred after 25 minutes.

2. Base Deblocking of 9-Xanthenylmethyl Phenylacetate: a. In Piperdine Solution: To a solution of 13.39 mg of 9-XM-phenylacetate in 1.6 mL of DMF was added 0.4 mL (100 eq.) of piperidine. The mixture was stirred at room temperature. TLC analysis with an eluant consisting of Skelly B—ether (2:1) showed no change after 2 days. b. In DBU Solution: To a solution of 6.36 mg of 9-XM-phenylacetate in 0.9 mL of DMF was added 0.3 mL of 1,8-diazabicyclo[5,4,0]-undec-7-ene (DBU) (100 eq.). The mixture was stirred at room temperature. TLC analysis with an eluant consisting Skelly B—ethyl acetate (3:1) showed that the deblocking was complete within 90 minutes. c. In TBD Solution: To a solution of 7.91 mg of 9-XM-phenylacetate in 0.3 mL of pyridine was added 100 mg (30 eq.) of 1,5,9-triazabicyclo[4,4,0]-dec-5-ene. The mixture was stirred at room temperature. TLC analysis with an eluant consisting of Skelly B—EtOAc (3:1) showed that the deblocking was complete within 27 minutes.

3. Stability of Xanthenylmethyl p-Chlorocarbanilate in Trifluoroacetic Acid: To a solution of 35.61 mg of Xmoc-PCA in 0.2 mL of deuterated chloroform was added 0.3 mL (40 eq.) of trifluoroacetic acid. The mixture was transferred to an NMR tube and allowed to stand at room temperature. The reaction was monitored by NMR spectroscopy (Varian A-60A, 60 MHz) and TLC with an eluant consisting of Skelly B—ethyl acetate (4:1). No change was noted after 3 days.

4. Stability of 9-Xanthenylmethyl Phenylacetate in Trifluoroacetic Acid: To a solution of 21.4 mg of 9-XM phenylacetate in 0.2 mL of deuterated chloroform was added 0.2 mL (40 eq.) of trifluoroacetic acid. The mixture was transferred to an NMR tube and let stand at room temperature. The reaction was monitored by NMR (Varian A-60A, 60 MHz) spectroscopy and TLC analysis with an eluant consisting of Skelly B—ether (2:1). No change was noted after 3 days.

5. Stability of 9-Xanthenylmethyl Carbanilate Towards Catalytic Hydrogenolysis: To a solution of 300 mg of Xmoc-aniline in 30 mL of EtOAc and 10 mL of 100% EtOH was added 30 mg of 5% palladium on charcoal and 30 mg of palladium acetate. The mixture was shaken under hydrogen at a pressure of 40 psi in a Parr apparatus for 24 hours. TLC analysis of the reaction mixture showed that the urethane remained intact. The catalyst was removed by filtration and the filtrate was evaporated under reduced pressure to give 283 mg (94.3%) of the recovered urethane as a white solid, m.p. 178°–181° C., the $^1$H NMR and IR spectra of which matched that of an authentic sample.

B. 9,10-Dihydro-9-anthracenylmethyl derivatives

1. Stability of 9,10-Dihydro-9-anthracenylmethyl p-Chlorocarbanilate in Trifluoroacetic Acid: To a solution of 23.61 mg of DHAmoc-PCA in 0.2 mL of deuterated chloroform was added 0.2 mL (40 eq.) of trifluoroacetic acid. The mixture was transferred to an NMR tube and allowed to stand at room temperature. The reaction was monitored by NMR spectroscopy (Varian A-60A, 60 MHz) and TLC with an eluant consisting of Skelly B—EtOAc (3:1). No change was noted after 4 days.

C. Comparison of 9-Xanthenylmethyl derivatives and 9,10-Dihydro-9-anthracenylmethyl derivatives 1. General Procedure for Studying the Stabilities of DHAmoc-PCA, Xmoc-PCA, and DC-Xmoc-PCA in Piperidine Solution To a solution of urethane (0.0294 mmol) in 1.2 mL of DMF was added 0.3 mL (2.94 mmol, 100 eq.) of piperidine. The mixture was stirred at room temperature and monitored by TLC with an eluant consisting of Skelly B—EtOAc (3:1). Evidence for initiation of the deblocking required 2 minutes for DC-Xmoc-PCA, 3.5 hours for Xmoc-PCA, and 7 hours for DHAmoc-PCA.

2. General Procedure for Studying the Deblocking of Xmoc-PCA and DHAmoc-PCA in DBU Solution: To a solution of urethane (0.0324 mmol) in 0.5 mL of DMF was added 0.5 mL (3.24 mmol, 100 eq.) of 1,8-diazabicyclo[5,4,0]undec-7-ene. The mixture was stirred at room temperature and monitored by TLC with the eluant consisting of Skelly B—EtOAc (3:1). The time needed to complete the deblocking was 3.5 hours for Xmoc-PCA, and 6 hours for DHAmoc-PCA.

EXAMPLE 58

Substituted FMOC derivatives

A. General Base Deblocking and Stability

1. General Procedure for Studying the Base Deblocking of the Urethanes Fmoc-PCA, BTS-Fmoc-PCA, DT-Fmoc-PCA, and TMS-Fmoc-PCA: A mixture of urethane (0.05 mmol) in a solution prepared from an equal volume of base (2.5 mmol, 50 eq.) and dichloromethane was stirred at room temperature. The course of the reaction was monitored by TLC with an eluant consisting of Skelly B—ether (3:1). Rates of deblocking and scavenging are summarized in Tables 2 and 3, respectively.

2. General Procedure for Studying the Base Deblocking of the Urethanes R-Fmoc-aniline (R=TMS, DMPS, DPMS, DT-TMS, TIPS): A solution of urethane (0.05 mmol) in a sample of redistilled base (5 mmol, 100 eq.) was allowed to stand at room temperature. The reaction was monitored periodically by TLC with an eluant consisting of Skelly B—$CH_2Cl_2$ (1:1). No reaction occurred according to the TLC test for urethanes having R=TIPS in the case of any of the bases tested after 24 hours. Results for the urethanes having other substituents are summarized in Tables 4 and 5. Table 4 shows the time needed for complete deblocking, whereas Table 5 shows the time needed for complete scavenging of the dibenzofulvene-type intermediate formed during the deblocking process.

3. General Procedure for Studying the Deblocking of Urethanes R-Fmoc-aniline (R=TMS, DMPS, DPMS, TIPS, DT-TMS) by Reaction with Fluoride Ion: To a solution of urethane (0.0513 mmol) in 0.7 mL of acetonitrile was added 45 mg (0.154 mmol, 3.0 eq.) of tetra-n-butyl-ammonium chloride and 20 mg (0.213 mmol, 4.1 eq.) of potassium fluoride dihydrate. The mixture was stirred at room temperature, the reaction being monitored by TLC with an eluant consisting of Skelly B—$CH_2Cl_2$ (1:1). The results are summarized in Table 6.

B. Piperidine Cleavage

1. Piperidine Cleavage of 2,7-Bis(trimethyl silyl)-9-fluorenylmethyl p-Chlorocarbanilate: A solution of 0.4 g of BTS-Fmoc-PCA in 7.6 mL of piperidine was stirred at room temperature for 30 minutes and poured into 125 mL of cold water. The precipitate was removed by filtration and the filtrate was extracted with ether (3×50 mL). The combined organic extracts were dried over anhydrous $MgSO_4$, and the solvent was evaporated under reduced pressure to give 0.10 g (96.9%) of a yellow solid, identified by NMR spectroscopy as p-chloroaniline. The solid (0.31 g, 94.0%, m.p. 105°–108° C.) precipitated from the original solution by the addition of water was recrystallized from methanol to give 0.25 g (75.8%) of N-[2,7-bis(trimethylsilyl)-9-fluorenyl-methyl]-piperidine, m.p. 107°–108° C.; $^1$H NMR ($CDCl_3$): δ 0.32 (s, 18H, $SiMe_3$), 1.47–1.80 (m, 6H, $CH_2CH_2CH_2$), 2.50–2.68 (m, 6H, $CH_2N$), 4.05 (t, 1H, CH), 7.43–7.96 (m, 6H, aryl).

Anal. Calcd for $C_{25}H_{37}NSi_2$: C, 73.64; H, 9.15; N, 3.44. Found: C, 73.38; H, 8.94; N, 3.35.

2. Piperidine Cleavage of 9-Trimethylsilyl-9-fluorenylmethyl p-Chlorocarbanilate: A solution of 0.4 g of TMS-Fmoc-PCA in 9.0 mL of piperidine was stirred at room temperature for 2.5 hours and poured into 140 mL of water. The precipitate was filtered and the filtrate was extracted with ether (3×50 mL). The combined ether extracts were dried over $MgSO_4$ and the solvent was evaporated under reduced pressure to give 0.12 g (99.1%) of a yellow solid which was identified by NMR analysis as p-chloroaniline. The solid precipitated from the original solution by the addition of water was recrystallized from Skelly B to give 0.23 g (92.1%) of N-(9-fluorenylmethyl)piperidine m.p. 118°–119° C.; $^1$H NMR ($CDCl_3$): δ 1.45–1.85 (m, 6H, $CH_2CH_2CH_2$), 2.48–2.69 (m, 6H, $CH_2N$), 4.07 (t, 1H, CH), 7.20–7.85 (m, 8H, aryl).

3. Piperidine Cleavage of 2,7-Di-tert-butyl-9-fluorenylmethyl p-Chlorocarbanilate: A solution of 0.3 g of DT-Fmoc-PCA in 6.5 mL of piperidine was stirred at room temperature for 30 minutes and poured into 50 mL of cold water. The suspended mixture was stirred for 20 minutes and the precipitate was removed by filtration, rinsed with water (2×5 mL), and dried in air to give 0.24 g (98.0%) of the crude N-(2,7-di-tert-butyl-9-fluorenylmethyl)piperidine as an off-white solid. Recrystallization from $CH_3OH$—$CHCl_3$ (2:1) afforded 0.20 g (82.01%)of the pure amine as white needles, m.p. 159°-160° C.; $^1H$ NMR ($CDCl_3$): δ 1.42 (s, 18H, t-Bu), 1.50-1.82 (m, 6H, $CH_2CH_2CH_2$), 2.55-2.70 (m, 6H, $CH_2N$), 4.02 (t, 1H, CH), 7.34-7.82 (m, 6H, aryl).

Anal. Calcd for $C_{27}H_{37}N$: C, 86.34; H, 9.93. Found: C, 86.57; H, 9.84.

4. Piperidine Cleavage of 2,7-Di-tert-butyl-9-trimethylsilyl-9-fluorenylmethyl Carbanilate: A solution of 0.4 g of DT-Fmoc-analine in 8.0 mL of piperidine was stirred at room temperature for 22 hours. The mixture was poured into 50 mL of cold water and stirred for 10 minutes. The precipitate was removed by filtration, rinsed with water (2×5 mL), and dried in air to afford 0.30 g (100%) of crude N-(2,7-di-tert-butyl-9-fluorenylmethyl)piperidine as an off-white solid. Recrystallization from $CH_3OH$—$CHCl_3$ (2:1) gave 0.248 g (82.53%) of the pure amine as white crystals, m.p. 159°-160° C., identified by mixture melting point, and IR and NMR spectral comparison with a sample obtained by piperidine cleavage of DT-Fmoc-PCA.

C. Acid Stability

1. General Procedure for Studying the stability of R-Fmoc-analine (R=TMS, DMPS, DPMS, DT-TMS, TIPS) in Trifluoroacetic Acid: To a solution of urethane (0.026 mmol) in 0.5 eg.) of trifluoroacetic acid. The mixture was stirred at room temperature and the course of the reaction was monitored by TLC with an eluant consisting of Skelly B—dichloromethane (1:1) to note the time needed for complete deblocking of the urethanes. The results are summarized in Table 7.

2. Stability of 2,7-Bis(trimethylsily)-9-fluorenylmethyl p-Chlorocarbanilate in Acetic Acid: To a solution preparation from 0.43 of BTS-Fmoc-PCA in 10 mL of methylene chloride was added 0.5 mL (10 eq.) of glacial acetic acid. The mixture was stirred at room temperature for 48 hours. TLC analysis showed no change. The mixture was washed with half sat'd $NaHCO_3$ (2×10 mL) and water (10 mL). The organic layer was dried over $MgSO_4$, filtered, and the solvent was evaporated in vacuo to give 0.41 g (95.35%) of the recovered urethane, m.p. 161°-163° C., the IR and $^1H$ NMR spectra of which matched that of an authentic sample.

3. Stability of 9-Trimethylsilyl-9-fluoromethyl p-Chlorocarbanilate in Acetic Acid: To a solution of 0.37 g of TMS-Fmoc-PCA in 10 mL of $CH_2Cl_2$ was added 0.5 mL (10 eq.) of glacial acetic acid. The mixture was stirred at room temperature. TLC analysis showed no change after 48 hours. The mixture was washed with half sat'd $NaHCO_3$ (2×10 mL) and $H_2O$ (10 mL). The organic layer was dried over anhydrous $MgSO_4$, filtered, and the solvent was evaporated in vacuo to give 0.361 g (97.5%) of the recovered urethane, m.p. 124°-126° C., the $^1H$ NMR and IR spectra of which matched that of an authentic sample.

4. Protolysis of 2,7-Bis(trimethylsilyl)-9-fluoroenylmethyl p-Chlorocarbanilate in Trifluoroacetic Acid: To a solution of 0.3 g of BTS-Fmoc-PCA in 8 mL of $CH_2Cl_2$ was added dropwise a solution of 0.5 mL (10.7 eq.) of trifluoroacetic acid in 3.0 mL of methylene chloride over a period of 10 minutes. The mixture was stirred at room temperature for 12 hours, washed with water (2×10 mL), and neutralized with sat'd $NaHCO_3$ (2×10 mL). The organic layer was dried over $MgSO_4$and the solvent was evaporated in vacuo to give 0.19 g (89.5%) of crude 9-fluorenylmethyl p-chlorocarbanilate. Recrystallization from EtOAc—Skelly B (2:1) gave 0.16 g (75.3%) of the pure urethane as colorless needles, m.p. 184°-185° C., identified by mixture melting point, and IR and NMR spectral comparisons with an authentic sample.

D. Stability to Catalytic Hydrogenation

1. Deblocking of 2,7-Bistrimethyl-silyl)-9-fluorenylmethyl Carbanilate: To a solution of 0.2 g BTS-Fmoc-aniline in 15 mL of 100% ethanol and 15 mL of EtOAc was added 20 mg of 10% palladium on charcoal at 0° C. The heterogeneous mixture was stirred under a hydrogen atmosphere (1 atm) for 20 hours. The catalyst was filtered and rinsed with EtOAc (2×5 mL). The combined filtrate was washed with sat'd $NH_4Cl$ (2×20 mL), water (20 mL), and dried over anhydrous $MgSO_4$. After evaporating the solvent in vacuo, the residue (0.14 g) was recrystallized from 95% ethanol to afford 0.11 g (78.0%) of 2,7-bis(trimethylsilyl)-9-methylfluorene as white needles, m.p. 106.5°-108° C., identified by mixture melting point, IR, and NMR spectral comparison with an authentic sample obtained as described above.

2. Stability of 9-Trimethylsilyl-9-fluorenylmethyl Carbanilate Towards Catalytic Hydrogenation: To a mixture of 0.15 g of TMS-Fmoc-analine and 0.15 g of BTS-Fmoc-analine in 20 mL of ethyl acetate and 30 mL of 100% ethanol was added 30 mg of 105 palladium on charcoal. The mixture was magnetically stirred at room temperature under a hydrogen atmosphere (1 atm) for 20 hours. The catalyst was removed by filtration and rinsed with EtOAc (2×5 mL). The filtrate was evaporated under reduced pressure to give an off-white oil which was chromatographed on silica gel (230–400 mesh, 2×40-cm packed column) with an eluant consisting of Skelly B—ether (4:1), to give as a first fraction 0.11 g (100%) of 2,7-bis(trimethylsilyl)-9-methylfluorene as a white solid, and as the second fraction 0.14 g (93.3%) of recovered TMS-Fmoc-analine as a white solid. Recrystallization of the former from 95% ethanol gave 78.3 mg (74.1%) of the pure silane, m.p. 107°-108.5° C. Recrystallization of the latter from Skelly B—ether (6:1) gave 0.126 g (84.0%) of the pure TMS-Fmoc-aniline as white needles, m.p. 137°-138° C., identified by mixture melting point, IR and NMR spectral comparison with an authentic sample.

TABLE 2

Time for Complete Deblocking of Substituted Urethanes (U-PCA) by Various Amines

| Base | $U^a =$ | | | |
|---|---|---|---|---|
| | $Fmoc^b$ | BTS-Fmoc | DT-Fmoc | TMS-Fmoc |
| Piperidine[c] | <3 min | <3 min | 12 min | 129 min |
| Ethanolamine | 45 min | 90 min | 4 hr | 150 min |
| Morpholine[c] | 75 min | 190 min | 10 hr | 13 hr |

TABLE 2-continued

Time for Complete Deblocking of
Substituted Urethanes (U-PCA) by Various Amines

| Base | $U^a =$ | | | |
|---|---|---|---|---|
| | Fmoc[b] | BTS-Fmoc | DT-Fmoc | TMS-Fmoc |
| t-Butylamine | 5 hr | 4.5 hr | 10 hr | >2 day |

[a]Abbreviations: Fmoc, 9-fluorenylmethoxycarbonyl; BTS-Fmoc, 2,7-bis(trimethylsilyl)-Fmoc; DT-Fmoc, 2,7-di-tert-butyl-Fmoc; TMS-Fmoc, 9-trimethylsilyl-Fmoc
[b]Included for comparison
[c]For these amines, a significant amount of the amino-dibenzofulvene type adduct had formed during the periods indicated (for completion of reaction, see Table 3).

TABLE 3

Time for Complete Scavenging of
Dibenzofulvene Analogs Derived from
Substituted Urethane (U-PCA) by Various Amines

| Base | $U^a =$ | | | |
|---|---|---|---|---|
| | Fmoc[b] | BTS-Fmoc | DT-Fmoc | TMS-Fmoc |
| Piperidine | 68 min | 40 min | 84 min | 195 min |
| Morpholine | 2.5 hr | 3.5 hr | 13 hr | 16.5 hr |

[a]See Table 2 for abbreviations
[b]Included for comparison

TABLE 4

Time for Complete Deblocking of
R-Fmoc-Aniline By Various Amines[a]

| Base | $U^b =$ | | | |
|---|---|---|---|---|
| | TMS | DMPS | DPMS | DT-TMS |
| Piperidine | 100 min | 40 min | 28 min | 13 hr |
| Morpholine | 180 min | 47 min | 35 min | 16 hr |
| t-Butylamine | 12 hr | 3.5 hr | 1.5 hr | >24 hr |

[a]For R = TIPS no reaction was detected by TLC after 24 hours.
[b]Abbreviations: TMS, 9-trimethylsilyl; DMPS, dimethylphenylsilyl; DPMS, diphenylmethylsilyl; DT-TMS, 2,7-di-tert-butyl-9-trimethylsilyl; TIPS, triisopropylsilyl

TABLE 5

Time for Complete Scavenging of Dibenzofulvene
Derived from R-Fmoc-aniline by Various Amines

| Base | $U^a =$ | | | |
|---|---|---|---|---|
| | TMS | DMPS | DPMS | DT-TMS |
| Piperidine | 300 min | 220 min | 150 min | 18 hr |
| Morpholine | 240 min | 60 min | 51 min | 17 hr |

[a]See Table 4 for abbreviations

TABLE 6

Time for Complete Deblocking
of R-Fmoc-aniline by Fluoride Ion

| | $R^a =$ | | | | |
|---|---|---|---|---|---|
| | TMS | DMPS | DPMS | TIPS | DT-TMS |
| Time | 5 min | <2 min | <2 min | 18 hr | 10 min |

[a]See Table 4 for abbreviations

TABLE 7

Time for Complete Deblocking of
R-Fmoc-aniline by Trifluoroacetic Acid

| | $R^a =$ | | | | |
|---|---|---|---|---|---|
| | TMS | DMPS | DPMS | TIPS | DT-TMS |
| Time | 5 hr | 8 hr | 18 hr | 34 min | 50 min |

[a]See Table 4 for abbreviations

EXAMPLE 59

Difluorenyl Derivatives

A. Base Deblocking of FM-Fmoc-PCA: 1. In Piperidine Solution: To a solution of 24.96 mg of FM-Fmoc-PCA in 0.5 mL of DMF was added 0.5 mL (100 eq.) of piperidine. The mixture was stirred at room temperature. TLC analysis showed that the first deblocking was detected after 12 hours. 2. In DBN Solution: To a solution of 12.81 mg of FM-Fmoc-PCA in 0.15 mL of DMF was added 0.15 mL (50 eq.) of 1,5-diazabicyclo[4,3,0]nonene-7 (DBN). The mixture was stirred at room temperature. TLC analysis showed that the deblocking reaction had begun within 10 minutes, but was still not complete after 24 hours. 3. In DBU Solution: To a solution of 10.58 mg of FM-Fmoc-PCA in 0.15 mL of DMF was added 0.15 mL (50 eq.) of 1,8-diazabicyclo[5,4,0]undec-7-ene (DBU). The mixture was stirred at room temperature. TLC analysis showed that the deblocking had begun within 10 minutes and was complete after 12 hours. 4. In TBD: To a solution of 18.95 mg of FM-Fmoc-PCA in 0.2 mL of DMF and 0.2 mL of pyridine was added 100 mg (20 eq.) of 1,5,9-triazabicyclo[4,4,0]dec-5-ene (TBD). The mixture was stirred at room temperature. TLC analysis showed that deblocking began immediately with the deblocking-scavenging reaction being complete after 1 hour.

B. Piperidine Deblocking of Bis(9-fluorenyl)methyl Carbanilate: To a suspension of 20 mg (0.042 mmol) of αF-Fmoc-analine in 0.2 mL of anhydrous ether was added 0.2 mL (2.02 mmol, 48.5 eq.) of piperidine. The mixture was stirred at room temperature and monitored by TLC with an eluant consisting of Skelly B—$CH_2Cl_2$ (1:1). The results showed that the urethane was totally decomposed within 10 minutes with the formation of at least four components. No attempt was made to isolate the individual component of the final reaction mixture.

C. Stability of FM-Fmoc-analine in Trifluoroacetic Acid: To a solution of 51.3 mg of FM-Fmoc-analine in 6 mL of $CHCl_3$ was added 4 mL (500 eq.) of trifluoroacetic acid. The mixture was stirred at room temperature and monitored by TLC with an eluant consisting of Skelly B—ether (2:1). No change was noted after two days. The mixture was diluted with 10 mL of chloroform, and washed with $H_2O$ (2×15 mL) and sat'd $NaHCO_3$ (2×15 mL). The organic layer was dried over $MgSO_4$ and the solvent was evaporated in vacuo to afford 49.8 mg (97.1%) of the recovered FM-Fmoc-analine as white solid, m.p. 241°-243° C., the $^1H$ NMR and IR spectra of which matched that of an authentic sample.

D. Stability of Bis(9-fluorenyl)methyl Carbanilate Towards Trifluoroacetic Acid: To a solution of 100 mg of α-F-Fmoc-analine in 12 mL of chloroform was added 8 mL (500 eq.) of trifluoroacetic acid. The mixture was stirred at room temperature and monitored by TLC with an eluant consisting of Skelly B—ether (2:1). No change was noted after 24 hours. The mixture was washed with water (2×10 mL), sat'd $NaHCO_3$ (3×10 mL), and water (10 mL). The organic layer was dried over $MgSO_4$ and the solvent was evaporated in vacuo to give 98.3 mg (98.3%) of the recovered urethane as a white solid, m.p. 223°-226° C. (dec.), the $^1H$ NMR and IR spectra of which matched that of an authentic sample.

E. Stability of FM-Fmoc-aniline Towards Catalytic Hydrogenolysis: To a mixture of 100 mg of FM-Fmoc-aniline and 63.9 mg of Fmoc-aniline in 30 mL of freshly distilled THF and 15 mL of 100% EtOH was added 30 mg of 5% palladium on charcoal. The mixture was shaken under hydrogen at a pressure of 45 psi in a Parr apparatus for 24 hours. The catalyst was filtered and the filtrate was evaporated in vacuo to give an oil which was chromatographed on silica gel (230–400 mesh, 2×40-cm packed column) with an eluant consisting of Skelly B—ether (3:1), to give a first fraction containing 36.2 mg (99.3) of the 9-methylfluorene derived from Fmoc-aniline, and a second fraction consisting of 99.4 mg (99.4%) of the recovered FM-Fmoc-aniline as a white solid. Recrystallization of the latter from ethyl acetate gave 89.1 mg (89.1%) of the pure FM-Fmoc-aniline as white crystals, m.p. 243°-244° C. the $^1$H NMR and IR spectra of which matched that of an authentic sample.

EXAMPLE 60

Amino Acid Derivatives

A. Base Deblocking of 9-Xanthenylmethoxycarbonyl-L-phenylalanine: 1. In DBU Solution: To a solution of 13.08 mg of Xmoc-Phe-Oh in 0.5 mL of DMF was added 0.5 mL of 1,8-diazabicyclo[5,4,0]-undec-7-ene (DBU, 100 eq.). The mixture was stirred at room temperature. The reaction was monitored by TLC with an eluant consisting of $CHCl_3$—$CH_3OH$—$CH_3CO_2H$ (9:1:0.1). Deblocking was complete after 36 hours. 2. In TBD Solution: To a solution of 7.25 mg of Xmoc-Phe-OH in 0.1 mL of pyridine and 0.1 mL of DMF was added 50 mg (20 eq.) of 1,5,9-triazabicyclo[4,4,0]dec-5-ene (TBD). The mixture was stirred at room temperature and monitored by TLC with an eluant consisting of $CHCl_3$—$CH_3OH$—$CH_3CO_2H$ (9:1:0.1). Deblocking was complete after 4.5 hours.

B. HPLC Monitoring of the Deblocking of $N^\epsilon$-(9-Xanthenylmethoxycarbonyl)-L-lysine by TBD: A mixture of 21.68 of H-Lys(Xmoc)-OH and 150 mg (20 eq.) of 1,5,9-triazabicyclo[4,4,0]dec-5-ene (TBD) in 0.3 mL of pyridine and 0.3 mL of DMF was stirred at room temperature. A 20 μL portion of the mixture was neutralized with a solution of 0.3 mL of 5% HCl and 0.3 mL of methanol, filtered, and injected for HPLC analysis which was carried out on a Waters Radial Pak 10-μm $C_{18}$ reverse phase column (0.8×10 cm) under the following conditions:

Mobile phase: 65% methanol and 35% TFA (0.1% in water)
Flow rate: 1 mL/minute
Injection volume: 5 μL
Detector: 254 nm The retention times were 7.66 min for H-Lys(Xmoc)-OH, and 14.20 min for the olefin. The results showed that no starting material was left after 4.5 hours.

We claim:

1. A compound of the formula

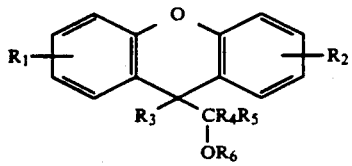

wherein $R_1$ and $R_2$ are independently hydrogen, lower alkyl, monoorganosilyl, diorganosilyl, triorganosilyl, halogen, aryl, or nitro;

$R_3$ is hydrogen, lower alkyl, monoorganosilyl, diorganosilyl, triorganosilyl, halogen, 9-fluorenylalkyl, cycloalkyl, aryl or aralkyl;

$R_4$ and $R_5$ are independently hydrogen, ethyl, propyl, isopropyl, butyl, sec-butyl, isobutyl, t-butyl, pentyl, isopentyl, neopentyl, hexyl, 1-naphthyl, 2-naphthyl or one of $R_4$ and $R_5$ is 9-fluorenyl and the other is hydrogen, ethyl, propyl, isopropyl, butyl, sec-butyl, isobutyl, t-butyl, pentyl, isopentyl, neopentyl, hexyl, 1-naphthyl or 2-naphthyl;

$R_6$ is H or COZ wherein Z is an amino acid, a peptide residue or a leaving group; and with the proviso that $R_1$, $R_2$, $R_3$, $R_4$, $R_5$ and $R_6$ are not all simultaneously H.

2. A compound of the formula

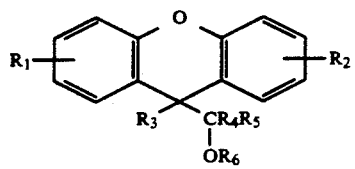

wherein $R_1$ and $R_2$ are independently hydrogen, lower alkyl, monoorganosilyl, diorganosilyl, triorganosilyl, halogen, aryl, or nitro;

$R_3$ is hydrogen, lower alkyl, monoorganosilyl, diorganosilyl, triorganosilyl, halogen, 9-fluorenylalkyl, cycloalkyl, aryl or aralkyl;

$R_4$ and $R_5$ are independently hydrogen, lower alkyl, aryl or one of $R_4$ and $R_5$ is 9-fluorenyl and the other is hydrogen, lower alkyl or aryl;

$R_6$ is H or COZ wherein Z is an amino acid, a peptide residue or a leaving group; and with the proviso that $R_1$, $R_2$, $R_3$, and $R_6$ are not all simultaneously H.

3. The compound of claim 1 or 2, wherein $R_4$ and $R_5$ are hydrogen.

4. The compound of claim 1 or 2, wherein 9-fluorenylalkyl of $R_3$ is 9-fluorenylmethyl.

5. The compound of claim 1 or 2, wherein $R_1$ and $R_2$ are independently hydrogen, lower alkyl, triorganosilyl, or halogen; $R_3$ is hydrogen, lower alkyl, triorganosilyl, or halogen; and $R_4$ and $R_5$ are hydrogen.

6. The compound of claim 1 or 2 wherein the organo groups of triorganosilyl are independently lower alkyl or aryl groups.

7. The compound of clam 1 or 2 wherein $R_6$ is COZ.

8. The compound of claim 7 wherein Z is halo, CN, $SR_{10}$, $SAr$, $N_3$, OAryl,

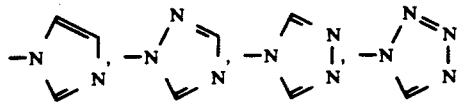

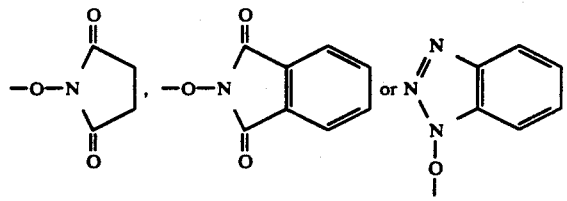

$R_{10}$ is lower alkyl, aryl or aralkyl, wherein the alkyl or aryl groups are unsubstituted, or mono- or disubstituted with halides, $SOR_{11}$, $SOR_{11}$ $COOR_{11}$, CHO, $COR_{11}$, CN, $CF_3$, or $NO_2$, and $R_{11}$ is lower alkyl or aryl.

9. The compound of claim 8, wherein Z is halo.

10. The compound of claim 9, wherein halo is Cl.

11. The compound of claim 8, wherein Z is $N_3$, O-succinimide or OAryl.

12. The compound of claim 7, wherein Z is an amino acid residue or a peptide residue.

13. The compound of claim 12, wherein said amino aid is an alpha-amino acid.

14. The compound of claim 1 which is 2,7-dichloro-9-xanthenemethanol, 9-xanthenylmethyl chloroformate, 2,7-dichloro-9-xanthenylmethyl chloroformate, 9-xanthenylmethyl benzyl ether, or 2,7-dichloro-9-xanthenylmethyl benzyl ether.

15. The compound of claim 1 which is 9-xanthenylmethyl azidoformate or succinimidyl 9-xanthenylmethyl carbonate.

* * * * *

UNITED STATES PATENT AND TRADEMARK OFFICE
CERTIFICATE OF CORRECTION

PATENT NO. : 5,101,059
DATED : March 31, 1992
INVENTOR(S) : Louis A. Carpino, et al.

It is certified that error appears in the above-indentified patent and that said Letters Patent is hereby corrected as shown below:

Column 3, line 41: "R" should read as --$R_1$--
Column 6, line 67: "R" should read as --$R_1$--
Column 8, line 34: "ar" should read as --are--
Column 11, line 4: "N-BuLi" should read as --n-BuLi--
Column 15, line 49: "9-$FM_2$" should read as --9-$FM^2$--
Column 19, line 39: "(DBU ," should read as --(DBU),--
Column 20, line 35: delete "b"
Column 20, line 51: "NH ," should read as --NH),--
Column 21, line 1: delete "5"
Column 22, line 27: "s," should read as --(s,--
Column 23, line 14: "$cm^1H$" should read as --$CM^{-1}$; $^1H$--
Column 23, line 35: "cm ; $^1H$" should read as --$cm^{-1}$; 1H--
Column 23, line 35: "5 3.59" should read as --$\delta$ 3.59--

UNITED STATES PATENT AND TRADEMARK OFFICE
CERTIFICATE OF CORRECTION

PATENT NO. : 5,101,059
DATED : March 31, 1992
INVENTOR(S) : Louis A. Carpino, et al.

It is certified that error appears in the above-indentified patent and that said Letters Patent is hereby corrected as shown below:

```
        Column 23, line 53:   "(C=))"  should read as
--(C=)--
        Column 23, line 54:   "5"  should read as --δ--
        Column 24, line 36:   "3,"  should read as --9,--
        Column 24, line 40:   "thiethylamine"  should read
as --triethylamine--
        Column 24, line 48:   "cm⁻¹; ¹NMR"  should read as
--cm⁻¹; ¹H NMR--
        Column 25, line 23:   "5 4.73"  should read as
-- δ 4.73--
        Column 25, line 63:   "NH)"  should read as --(NH)--
        Column 25, line 67:   after "For"  delete --Si:--
        Column 26, line 30:   "5-0.12"  should read as
-- δ -0.12--
        Column 27, line 36:   "50 mL)"  should read as
--(50 mL)--
        Column 27, line 65:   "4.26 ˢ"  should read as
--4.26 (s,--
        Column 28, line 19:   "(CDCL3 5 0.08"  should read
as --(CDCL₃): δ 0.08--
```

UNITED STATES PATENT AND TRADEMARK OFFICE
CERTIFICATE OF CORRECTION

PATENT NO. : 5,101,059
DATED : March 31, 1992
INVENTOR(S) : Louis A. Carpino, et al.

It is certified that error appears in the above-indentified patent and that said Letters Patent is hereby corrected as shown below:

Column 28, line 20: "C-CH$_{20}$)" should read as --(C-CH$_2$O)--

Column 29, line 33: "(3:1" should read as --(3:1)--

Column 29, lines 36-37: "3285 cm$^{-1}$;" should read as --3285 (NH), 1697 (C=O) cm$^{-1}$;--

Column 29, line 40: after "5.38;" insert --N, 2.79.--

Column 29, line 54: "SiMe$_{2, 5.07}$" should read as --SiMe$_2$), 5.07--

Column 30, line 9: "C27H24OSi:" should read as --C$_{27}$H$_{24}$OSi:--

Column 30, line 57: "S-CH" should read as --Si-CH--

Column 31, line 17: after "mixture" delete --O--

Column 31, line 68: delete "$^1$H NMR (CDCl$_3$) 5-0.10 (s,"

Column 32, line 45: "CHCH$_{20}$)" should read as --CHCH$_2$O)--

UNITED STATES PATENT AND TRADEMARK OFFICE
CERTIFICATE OF CORRECTION

PATENT NO. : 5,101,059
DATED : March 31, 1992
INVENTOR(S) : Louis A. Carpino, et al.

It is certified that error appears in the above-indentified patent and that said Letters Patent is hereby corrected as shown below:

Column 32, line 62: "(KBr" should read as --(KBr)--

Column 33, line 15: " 5 " should read as -- $\delta$ --

Column 33, line 44: "($CDC_{13}$)" should read as --($CHCl_3$)--

Column 33, line 52: "(trimethylsilyl]" should read as --(trimethylsilyl)--

Column 33, line 66: "$CHO_2$)" should read as --$CH_2O$)--

Column 34, line 19: delete "$^1H$ NMR ($CDCl_3$): $\delta$ -0.07"

Column 34, line 44: "C-$CH_{20}$)" should read as --C-$CH_2O$)--

Column 35, lines 23-24: "280." should read as --2.80--

Column 35, line 45: "CH-$CH_{20}$)" should read as --CH-$CH_2O$)--

Column 36, line 24: "CH-$CH_{20}$)" should read as --CH-$CH_2O$)--

Column 36, line 30: delete "15"

UNITED STATES PATENT AND TRADEMARK OFFICE
CERTIFICATE OF CORRECTION

PATENT NO. : 5,101,059
DATED : March 31, 1992
INVENTOR(S) : Louis A. Carpino, et al.

It is certified that error appears in the above-indentified patent and that said Letters Patent is hereby corrected as shown below:

Column 36, line 31: "Fluorenylmethyl]" should read as --Fluorenylmethyl)--

Column 36, line 66: "$CCH_{20}$)" should read as --$CCH_2O$)--

Column 37, line 15: "1700 =O)" should read as --1700 (C=O)--

Column 37, line 16: "$CH_{20}$)" should read as --$CH_2O$)--

Column 39, line 13: "38.6" should read as --39.6--

Column 39, line 28: "(4 1)" should read as --(4:1)--

Column 39, lines 29-30: delete "pure Fmoc-OSu as white needles, m.p."

Column 39, line 34: "$CH_{20}$)" should read as --$CH_2O$)--

Column 39, line 37: "Ns-" should read as --$N^{\epsilon}$- --

Column 39, line 57: "$^{23}23546$" should read as --$^{23}546$--

UNITED STATES PATENT AND TRADEMARK OFFICE
CERTIFICATE OF CORRECTION

PATENT NO. : 5,101,059            Page 6 of 7
DATED : March 31, 1992
INVENTOR(S) : Louis A. Carpino, et al.

It is certified that error appears in the above-indentified patent and that said Letters Patent is hereby corrected as shown below:

Column 40, line 54: "$CH_2C_{12}$)" should read as --$CH_2Cl_2$)--

Column 40, line 68: "Opfp): To" should read as --Opfp as--

Column 41, line 2: "CH)" should read as --$CH_2Cl_2$)--

Column 41, line 5: delete "24546 -2.9(c=1,"

Column 45, line 36: "0.5 eg.)" should read as --0.5 mL of methylene chloride was added 0.04 mL (0.52 mmol, 20 eg.)--

Column 45, line 45: "0.43 of" should read as --0.43 g of--

Column 46, line 40: "105" should read as --10%--

Column 49, line 4: "(99.3)" should read as --(99.3%)--

UNITED STATES PATENT AND TRADEMARK OFFICE
CERTIFICATE OF CORRECTION

PATENT NO. : 5,101,059
DATED : March 31, 1992
INVENTOR(S) : Louis A. Carpino, et al.

It is certified that error appears in the above-indentified patent and that said Letters Patent is hereby corrected as shown below:

Column 51, line 10, claim 13, "aid" should read --acid--.

Signed and Sealed this

First Day of November, 1994

Attest:

Attesting Officer

BRUCE LEHMAN

Commissioner of Patents and Trademarks